(12) United States Patent
Lim et al.

(10) Patent No.: US 11,158,818 B2
(45) Date of Patent: *Oct. 26, 2021

(54) COMPOUND AND ORGANIC SOLAR CELL COMPRISING SAME

(71) Applicant: LG CHEM, LTD., Seoul (KR)

(72) Inventors: Bogyu Lim, Daejeon (KR); Songrim Jang, Daejeon (KR); Doowhan Choi, Daejeon (KR); Ji Hoon Kim, Daejeon (KR)

(73) Assignee: LG CHEM, LTD.

( * ) Notice: Subject to any disclaimer, the term of this patent is extended or adjusted under 35 U.S.C. 154(b) by 0 days.

This patent is subject to a terminal disclaimer.

(21) Appl. No.: 16/472,355

(22) PCT Filed: Mar. 16, 2018

(86) PCT No.: PCT/KR2018/003091
§ 371 (c)(1),
(2) Date: Jun. 21, 2019

(87) PCT Pub. No.: WO2018/174476
PCT Pub. Date: Sep. 27, 2018

(65) Prior Publication Data
US 2019/0363262 A1    Nov. 28, 2019

(30) Foreign Application Priority Data

Mar. 21, 2017  (KR) .................. 10-2017-0035338
Mar. 15, 2018  (KR) .................. 10-2018-0030148

(51) Int. Cl.
C07D 495/04    (2006.01)
H01L 51/00     (2006.01)
H01L 51/42     (2006.01)
H01L 51/44     (2006.01)

(52) U.S. Cl.
CPC ........ *H01L 51/0074* (2013.01); *C07D 495/04* (2013.01); *H01L 51/0058* (2013.01); *H01L 51/0068* (2013.01); *H01L 51/0069* (2013.01); *H01L 51/4253* (2013.01); *H01L 51/442* (2013.01)

(58) Field of Classification Search
CPC . C07D 495/04; C07D 417/14; H01L 51/0074; H01L 51/0058; H01L 51/0068; H01L 51/0069; H01L 51/4253; H01L 51/442; H01L 51/0043; H01L 51/0036; H01L 51/4233; H01L 2251/308; H01L 51/0053; H01L 51/424; Y02E 10/549
See application file for complete search history.

(56) References Cited

U.S. PATENT DOCUMENTS

| | | | |
|---|---|---|---|
| 6,143,433 A | 11/2000 | Murata et al. | |
| 6,344,918 B1 | 2/2002 | Berneth et al. | |
| 7,445,855 B2 | 11/2008 | Mackenzie et al. | |
| 8,007,926 B2 | 8/2011 | Thompson et al. | |
| 9,190,626 B2 | 11/2015 | Joo et al. | |
| 9,391,281 B2 | 7/2016 | Lee et al. | |
| 9,540,374 B2 | 1/2017 | Park et al. | |
| 9,748,489 B2 | 8/2017 | Kim et al. | |
| 9,954,181 B2 | 4/2018 | Heo et al. | |
| 10,326,083 B2 | 6/2019 | Yagi et al. | |
| 10,381,569 B2 | 8/2019 | Xia et al. | |
| 10,662,313 B2 | 5/2020 | Choi et al. | |
| 10,756,276 B2 * | 8/2020 | Lim .................. | H01L 51/4253 |
| 2011/0049367 A1 | 3/2011 | Forrest et al. | |
| 2012/0119195 A1 | 5/2012 | Sagisaka et al. | |
| 2013/0042918 A1 | 2/2013 | Evans et al. | |
| 2013/0105768 A1 | 5/2013 | Leem et al. | |
| 2014/0131627 A1 | 5/2014 | Wang et al. | |
| 2014/0158949 A1 | 6/2014 | Wang et al. | |
| 2014/0252279 A1 | 9/2014 | Wang et al. | |
| 2015/0041727 A1 | 2/2015 | Wang et al. | |
| 2016/0372680 A1 | 12/2016 | Lim et al. | |
| 2017/0018724 A1 | 1/2017 | Tsuyama et al. | |
| 2017/0210752 A1 | 7/2017 | Mitchell et al. | |
| 2019/0378993 A1 | 12/2019 | Lim et al. | |
| 2020/0301230 A1 | 9/2020 | Lim et al. | |

FOREIGN PATENT DOCUMENTS

| | | |
|---|---|---|
| CN | 104557968 | 4/2015 |
| JP | 2009155648 | 7/2009 |
| JP | 2015059109 A | 3/2015 |
| JP | 2016065218 A | 4/2016 |
| KR | 1020010112380 | 12/2001 |
| KR | 1020080075663 A | 8/2008 |
| KR | 1020110132858 | 12/2011 |
| KR | 1020120043009 A | 5/2012 |
| KR | 1020130047367 A | 5/2013 |
| KR | 20140063579 | 5/2014 |
| KR | 1020140063608 A | 5/2014 |
| KR | 20140088571 | 7/2014 |
| KR | 20140135749 | 11/2014 |

(Continued)

OTHER PUBLICATIONS

Chemical Abstract Service STN Database, Registry No. 1817646-68-6 [Entered STN: Oct. 30, 2015]. (Year: 2015).*
Lin et al, A Facile Planar Fused-Ring Electron Acceptor for As-Cast Polymer Solar Cells with 8.71% Efficiency, Journal of the American Chemical Society, 2016, 138 (9), 2973-2976.
C.W. Tang, Two-layer organic photovoltaic cell, Appl. Phys. Lett., vol. 48, No. 2, 1986, pp. 183-185.

(Continued)

*Primary Examiner* — Amanda L. Aguirre
(74) *Attorney, Agent, or Firm* — Myers Bigel, P.A.

(57) ABSTRACT

The present specification provides the compound represented by Formula 1 and an organic solar cell including the same.

12 Claims, 6 Drawing Sheets

(56) References Cited

FOREIGN PATENT DOCUMENTS

| KR | 20150113631 | * | 10/2015 | |
|---|---|---|---|---|
| KR | 1020150113629 A | | 10/2015 | |
| KR | 1020150121661 A | | 10/2015 | |
| KR | 20160097766 | | 8/2016 | |
| KR | 20170003234 | | 1/2017 | |
| KR | 1020170038037 A | | 4/2017 | |
| WO | WO-2019066553 A2 | * | 4/2019 | ............ C08L 65/00 |

OTHER PUBLICATIONS

Yu et al, Polymer Photovoltaic Cells: Enhanced Efficiencies via a Network of Internal Donor-Acceptor Heterojunctions, Science, vol. 270, 1995, pp. 1789-1791.
International Search Report of the International Searching Authority corresponding to International Patent Application No. PCT/KR2018/003091, dated Jun. 22, 2018. (6 pages with English translation).
"International Search Report corresponding to PCT/KR2018/007567; dated Oct. 16, 2018 (5 pages with English translation)".
"International Search Report corresponding to PCT/KR2018/009524; dated Mar. 7, 2019 (5 pages with English translation)".
"International Search Report corresponding to PCT/KR2018/010895; dated Jan. 2, 2019 (5 pages with English translation)".
Lee, et al., ""Highly p-extended small molecules with bis(alkylthio)methylene side chains for organic field-effect transistors" Journal of Materials Chemistry C, 6: 7604-7611 (2018)".
Zhao, et al., ""Derivatives of 4,9-Dihydro-s-indaceno[1,2-b:5,6-b']dithiophene-4,9-dione: Synthesis and Properties" J. Org. Chem., 72(17):6364-6371 (2007)".

\* cited by examiner

COMPOUND AND ORGANIC SOLAR CELL COMPRISING SAME

CROSS-REFERENCE TO RELATED APPLICATIONS

This application is a National Stage Entry of International Application No. PCT/KR2018/003091 filed on Mar. 16, 2018, and claims the benefit of Korean Application Nos. 10-2017-0035338 and 10-2018-0030148 filed on Mar. 21, 2017 and Mar. 15, 2018, respectively, which Korean Applications are hereby incorporated by reference in their entirety for all purposes as if fully set forth herein.

TECHNICAL FIELD

The present specification relates to a compound and an organic solar cell including the same.

BACKGROUND ART

An organic solar cell is a device which may directly convert solar energy into electric energy by applying a photovoltaic effect. A solar cell may be divided into an inorganic solar cell and an organic solar cell, depending on the materials constituting a thin film. Typical solar cells are made through a p-n junction by doping crystalline silicon (Si), which is an inorganic semiconductor. Electrons and holes generated by absorbing light diffuse to p-n junction points and move to an electrode while being accelerated by the electric field. The power conversion efficiency in this process is defined as the ratio of electric power given to an external circuit and solar power entering the solar cell, and the efficiency have reached approximately 24% when measured under a currently standardized virtual solar irradiation condition. However, since inorganic solar cells in the related art have already shown the limitation in economic feasibility and material demands and supplies, an organic semiconductor solar cell, which is easily processed and inexpensive and has various functionalities, has come into the spotlight as a long-term alternative energy source.

For the solar cell, it is important to increase efficiency so as to output as much electric energy as possible from solar energy. In order to increase the efficiency of the solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases, and accordingly, manufacturing costs may be increased.

DETAILED DESCRIPTION OF THE INVENTION

Technical Problem

An object of the present specification is to provide a compound and an organic solar cell including the same.

Technical Solution

An exemplary embodiment of the present specification provides a compound represented by the following Formula 1.

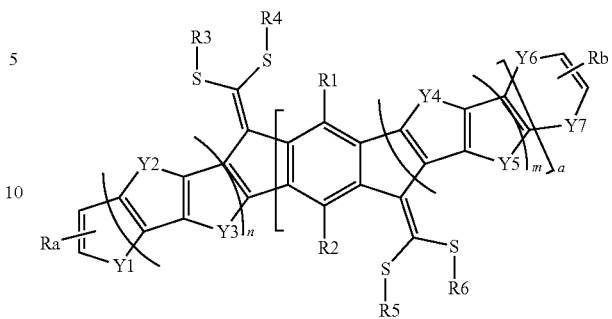

[Formula 1]

In Formula 1,

Ra and Rb are the same as or different from each other, and are each independently a group which serves as an electron withdrawing group, Y1 to Y5 are the same as or different from each other, and are each independently CRR', NR, O, SiRR', PR, S, GeRR', Se, or Te, Y6 and Y7 are different from each other, and are each independently a direct bond, CRR', NR, O, SiRR', PR, S, GeRR', Se, or Te, a is 0 or 1, when a is 0, Y6 is a direct bond, and Y7 is CRR', NR, O, SiRR', PR, S, GeRR', Se, or Te, when a is 1, Y7 is a direct bond, and Y6 is CRR', NR, O, SiRR', PR, S, GeRR', Se, or Te, n and m are each an integer from 0 to 5, when n and m are each 2 or more, the structures in the parenthesis are the same as or different from each other, and R1 to R6, R, and R' are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

Another exemplary embodiment of the present specification provides an organic solar cell including: a first electrode;

a second electrode provided to face the first electrode; and an organic material layer having one or more layers provided between the first electrode and the second electrode and including a photoactive layer, in which one or more layers of the organic material layer include the compound.

Advantageous Effects

For a compound according to an exemplary embodiment of the present specification, Sulfur (S) may be introduced into an alkyl chain. Accordingly, crystallinity due to the chalcogen-chalcogen interaction in the molecule may be improved.

The compound according to an exemplary embodiment of the present specification is an electron acceptor material, and may be used as a material for an organic material layer alone without fullerenes, and an organic solar cell including the same may exhibit characteristics which are excellent in an increase in open-circuit voltage and short-circuit current and/or an increase in efficiency, and the like.

The compound according to an exemplary embodiment of the present specification has excellent oxidation stability and thus has an excellent service life when applied to a device.

Figure 1:
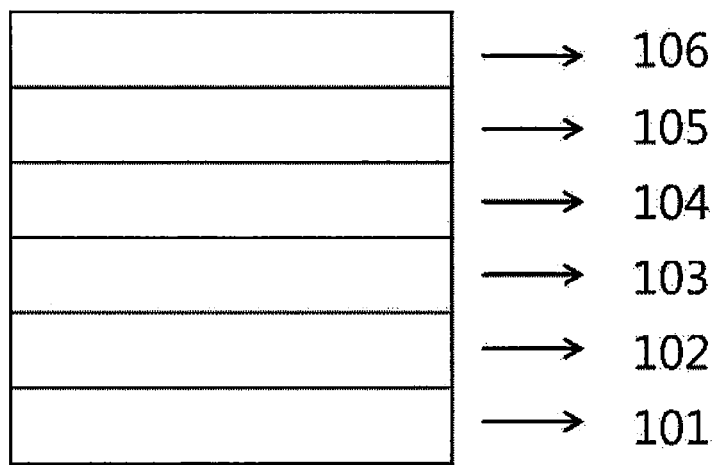
FIG. 1 is a view illustrating an organic solar cell according to an exemplary embodiment of the present specification.

101: Substrate
102: First electrode
103: Electron transport layer
104: Photoactive layer
105: Hole transport layer
106: Second electrode

BEST MODE

Hereinafter, the present specification will be described in detail.

An exemplary embodiment of the present specification provides the compound represented by Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a siloxane group; a boron group; an amine group; an arylphosphine group; a phosphine oxide group; an aryl group; and a heterocyclic group, or being substituted with a substituent to which two or more substituents among the exemplified substituents are linked or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion.

In the present specification, a halogen group may be fluorine, chlorine, bromine or iodine.

In the present specification, the number of carbon atoms of an imide group is not particularly limited, but is preferably 1 to 30. Specifically, the imide group may be a compound having the following structures, but is not limited thereto.

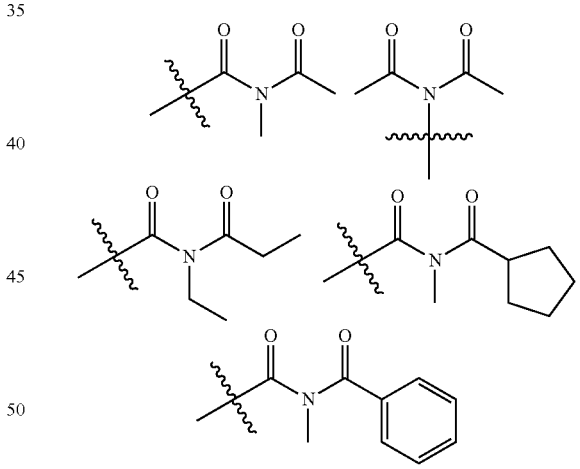

In the present specification, for an amide group, the nitrogen of the amide group may be substituted with hydrogen, an alkyl group having 1 to 30 carbon atoms, or an aryl group having 6 to 30 carbon atoms. Specifically, the amide group may be a compound having the following structural formulae, but is not limited thereto

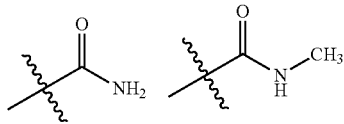

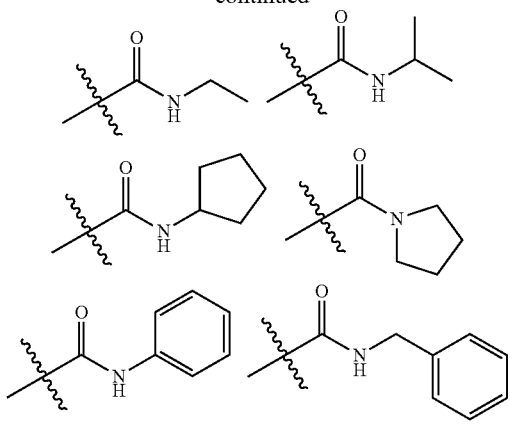

In the present specification, the number of carbon atoms of a carbonyl group is not particularly limited, but is preferably 1 to 30. Specifically, the carbonyl group may be a compound having the following structures, but is not limited thereto.

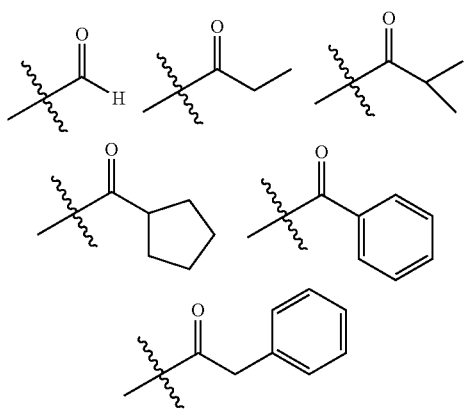

In the present specification, for an ester group, the oxygen of the ester group may be substituted with an alkyl group having 1 to 25 carbon atoms, a cycloalkyl group having 3 to 30 carbon atoms, or an aryl group having 6 to 30 carbon atoms. Specifically, the ester group may be a compound having the following structural formulae, but is not limited thereto.

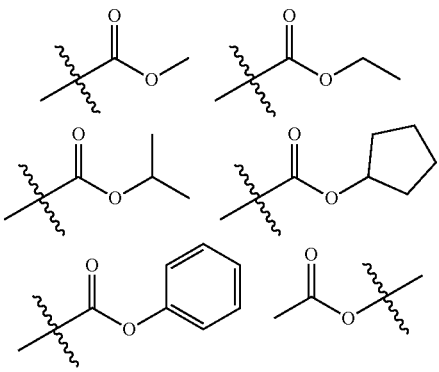

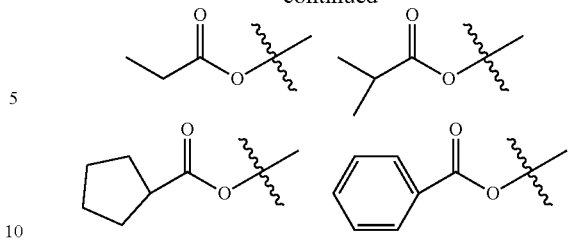

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tort-pentyl, hexyl, n-hexyl, 1-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methyl cyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group may be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH$_2$; an alkylamine group; an N-arylalkylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, the alkyl group in the alkylamine group, the N-arylalkylamine group, the alkylthioxy group, the alkylsulfoxy group, and the N-alkylheteroarylamine group is the same as the above-described examples of the alkyl group.

In the present specification, the alkenyl group may be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyl dimethyl silyl group, a propyldimethylsilyl group, a triphenylsilyl group, a diphenylsilyl group, a phenylsilyl group, and the like, but are not limited thereto.

In the present specification, a boron group may be $-BR_{100}R_{200}$, and $R_{100}$ and $R_{200}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthyiphosphine oxide, and the like, but are not limited thereto.

In the present specification, an aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terephenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heterocyclic group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and the heterocyclic group may be monocyclic or polycyclic. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a phenothiazinyl group, a dibenzofuranyl group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroaryl amine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, the heteroaryl group in the N-arylheteroarylamine group and the N-alkyl heteroarylamine group is the same as the above-described examples of the heteroaryl group.

In an exemplary embodiment of the present specification, n and m are each an integer from 0 to 5.

In an exemplary embodiment of the present specification, n and m are each an integer from 0 to 4.

In an exemplary embodiment of the present specification, n and m are each an integer from 0 to 3.

In an exemplary embodiment of the present specification, n and m are each an integer from 0 to 2.

In an exemplary embodiment of the present specification, n and m are each 0 or 1.

In an exemplary embodiment of the present specification, the compound represented by Formula 1 may be symmetric with respect to a benzene ring.

In an exemplary embodiment of the present specification, the compound represented by Formula 1 may be represented by the following Formula 2 or 3.

[Formula 2]

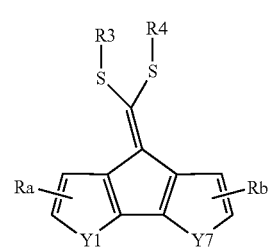

-continued

[Formula 3]

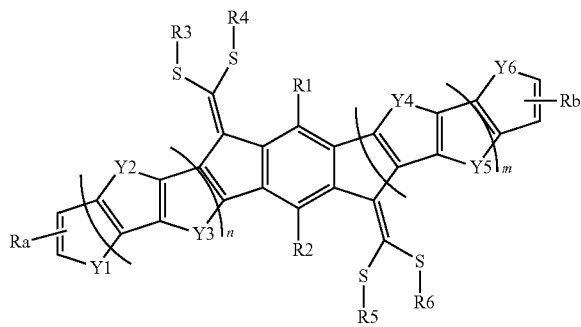

[Formula 1-2]

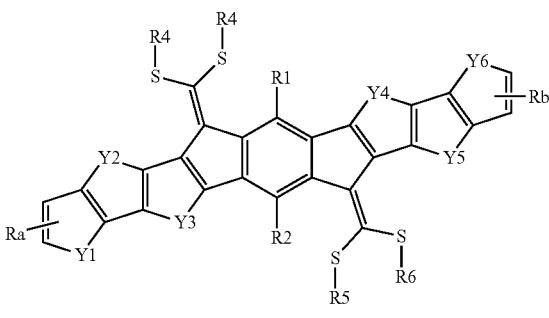

In Formula 2 or 3,

Ra and Rb are the same as or different from each other, and are each independently a group which serves as an electron withdrawing group, Y1 to Y5 are the same as or different from each other, and are each independently CRR', NR, O, SiRR', PR, S, GeRR', Se, or Te, Y6 and Y7 are different from each other, and are each independently a direct bond, CRR', NR, O, SiRR', PR, S, GeRR', Se, or Te, n and m are each an integer from 0 to 5, when n and m are each 2 or more, the structures in the parenthesis are the same as or different from each other, and R1 to R6, R, and R' are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In an exemplary embodiment of the present specification, Formula 3 may be represented by the following Formula 1-1 or 1-2.

[Formula 1-1]

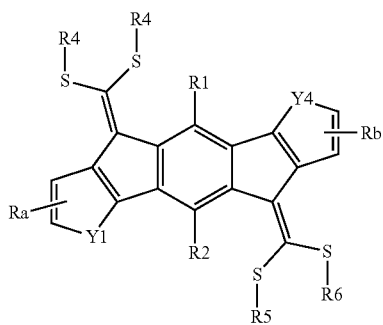

In Formula 1-1 or 1-2,

Ra and Rb are the same as or different from each other, and are each independently a group which serves as an electron withdrawing group, Y1 to Y6 are the same as or different from each other, and are each dependently CRR', NR, O, SiRR', PR, S, GeRR', Se, or Te, and R1 to R6, R, and R' are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In an exemplary embodiment of the present specification, when a, n, and m of Formula 1 are each 0, Formula 1 may be represented by Formula 2.

In an exemplary embodiment of the present specification, when a of Formula 1 is 1, Formula 1 may be represented by Formula 3.

In an exemplary embodiment of the present specification, when a of Formula 1 is 1, and n and m of Formula 1 are each 0, Formula 1 may be represented by Formula 1-1.

In an exemplary embodiment of the present specification, when a, n, and m of Formula 1 are each 1, Formula 1 may be represented by Formula 1-2.

In an exemplary embodiment of the present specification, when n and in of Formula 3 are each 0, Formula 3 may be represented by Formula 1-1.

In an exemplary embodiment of the present specification, when n and m of Formula 3 are each 1, Formula 3 may be represented by Formula 1-2.

In an exemplary embodiment of the present specification, Ra and Rb are any one of the following structures.

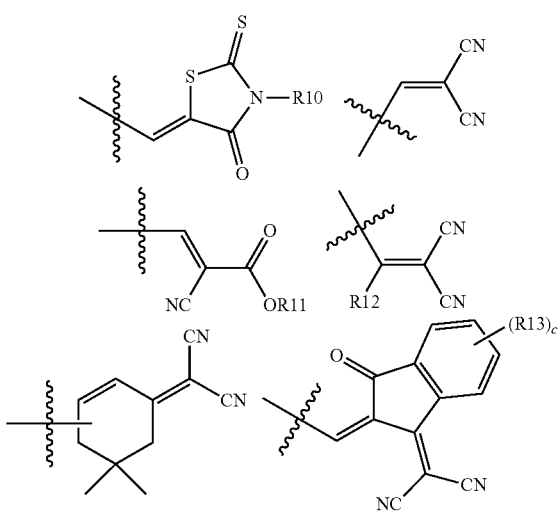

In the structures, c is an integer from 1 to 4, when c is 2 or more, the structures in the parenthesis are the same as or different from each other, and R10 to R13 are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In an exemplary embodiment of the present specification, R1 and R2 are the same as or different from each other, and are each independently hydrogen; a halogen group; a substituted or unsubstituted alkyl group; a substituted or unsubstituted alkoxy group; a substituted or unsubstituted aryl group; or a substituted or unsubstituted heterocyclic group.

In an exemplary embodiment of the present specification, R1 and R2 are hydrogen.

In an exemplary embodiment of the present specification, R10 to R13 are the same as or different from each other, and are each independently hydrogen; a halogen group; a nitrile group; an amide group; a hydroxyl group; a substituted or unsubstituted alkyl group; a substituted or unsubstituted cycloalkyl group; a substituted or unsubstituted alkoxy group; a substituted or unsubstituted aryl group; or a substituted or unsubstituted heterocyclic group.

In an exemplary embodiment of the present specification, R10 to R13 are the same as or different from each other, and are each independently hydrogen; a halogen group; a substituted or unsubstituted alkyl group; a substituted or unsubstituted aryl group; or a substituted or unsubstituted heterocyclic group.

In an exemplary embodiment of the present specification, R10 and R13 are the same as or different from each other, and are each independently hydrogen; a halogen group; or a substituted or unsubstituted alkyl group.

In an exemplary embodiment of the present specification, R10 is a substituted or unsubstituted alkyl group.

In an exemplary embodiment of the present specification, R10 is a substituted or unsubstituted alkyl group having 1 to 30 carbon atoms.

In an exemplary embodiment of the present specification, R10 is a substituted or unsubstituted alkyl group having 1 to 20 carbon atoms.

In an exemplary embodiment of the present specification, R10 is a substituted or unsubstituted alkyl group having 1 to 10 carbon atoms.

In an exemplary embodiment of the present specification, R10 is an alkyl group having 1 to 10 carbon atoms.

In an exemplary embodiment of the present specification, R13 is hydrogen or a halogen group.

In an exemplary embodiment of the present specification, R13 is hydrogen or fluorine.

In an exemplary embodiment of the present specification, Ra and Rb are each

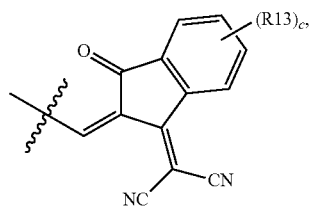

c is 4, and R13 is hydrogen.

In an exemplary embodiment of the present specification, Ra and Rb are each

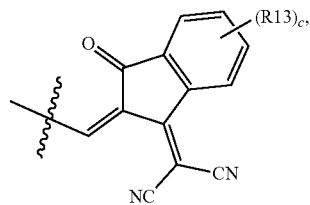

c is 2, and R13 is a halogen group.

In an exemplary embodiment of the present specification, Ra and Rb are each

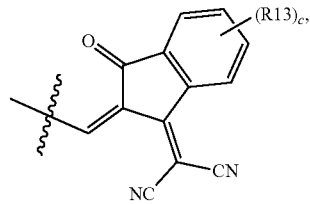

c is 2, and R13 is fluorine.

In an exemplary embodiment of the present specification, Ra and Rb are each

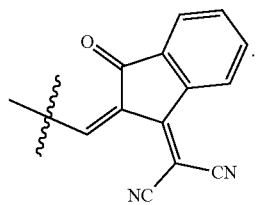 [SMILES: */C=C1\C(=O)c2ccccc2C1=C(C#N)C#N]

In an exemplary embodiment of the present specification, Ra and Rb are each

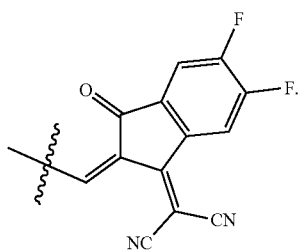 [SMILES: */C=C1\C(=O)c2cc(F)c(F)cc2C1=C(C#N)C#N]

In an exemplary embodiment of the present specification, Ra and Rb are each

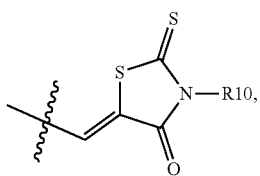

and R10 is an alkyl group having 1 to 10 carbon atoms.

In an exemplary embodiment of the present specification, Ra and Rb are each

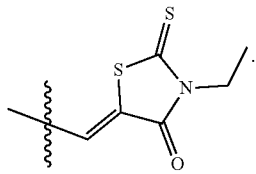 [SMILES: */C=C1\SC(=S)N(CC)C1=O]

In an exemplary embodiment of the present specification, Ra and Rb are each

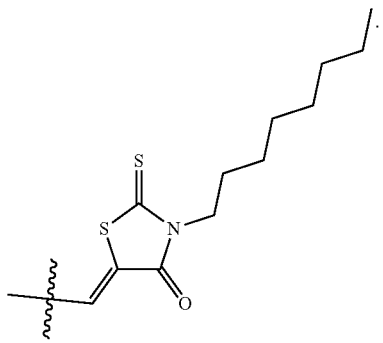 [SMILES: */C=C1\SC(=S)N(CCCCCCCC)C1=O]

In an exemplary embodiment of the present specification, Formula 1 may be represented by any one of the following Formulae 11-11 to 1-22.

[Formula 1-11]

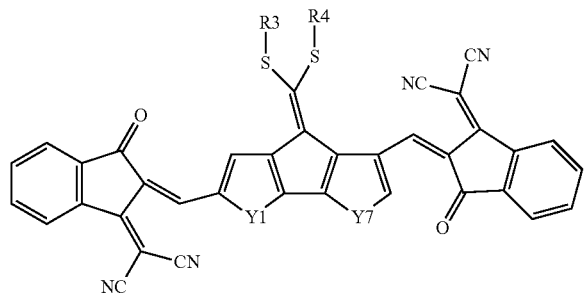

[Formula 1-12]

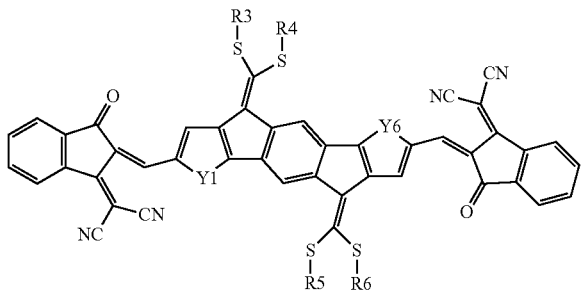

[Formula 1-13]

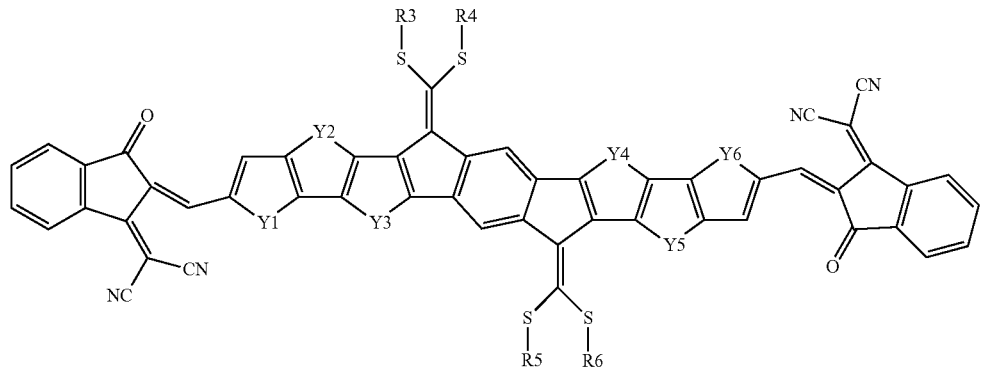

[Formula 1-14]
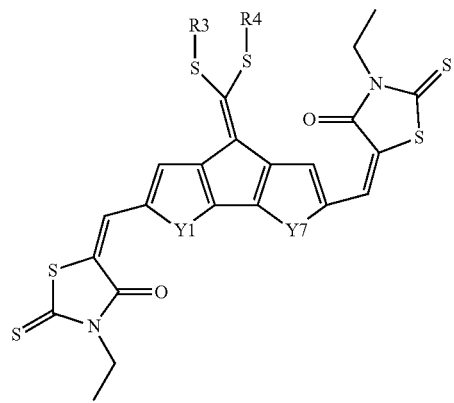
[Formula 1-15]
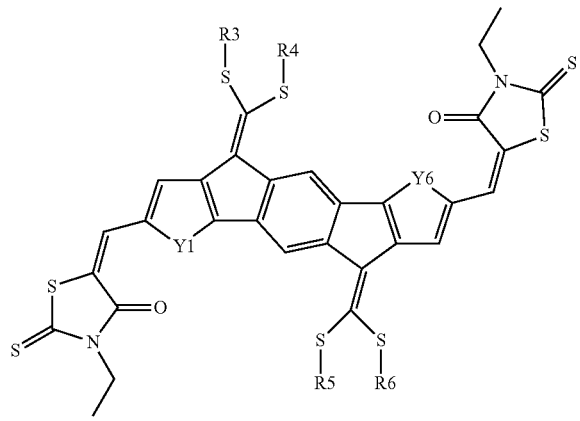
[Formula 1-16]
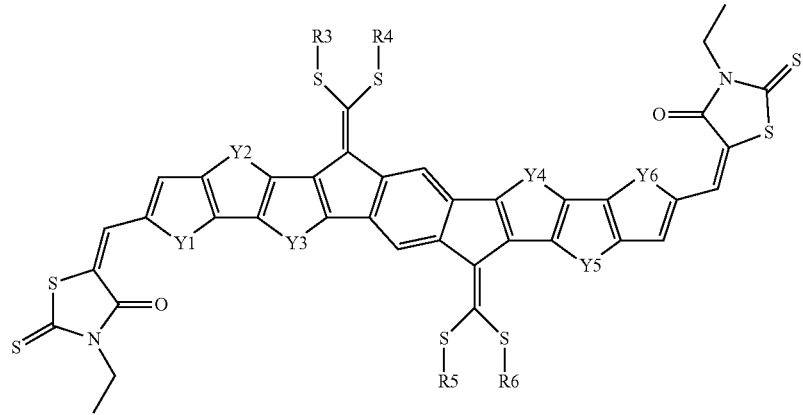
[Formula 1-17]
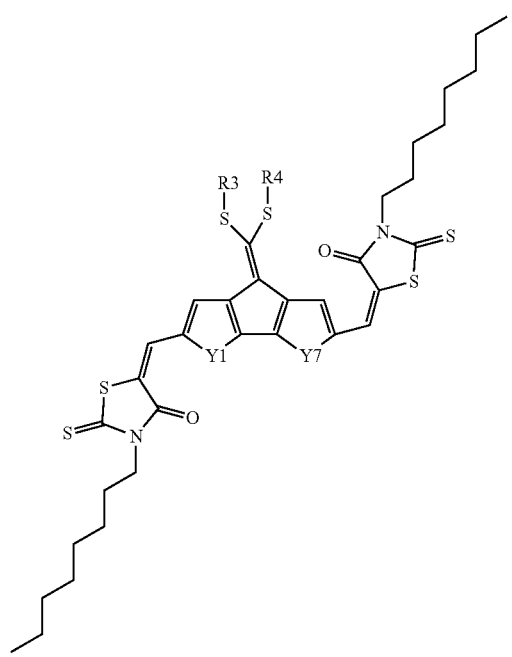
[Formula 1-18]
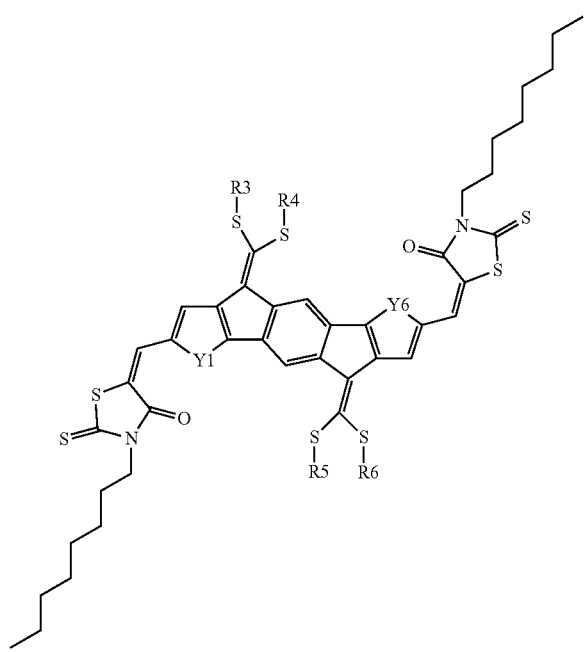

[Formula 1-19]
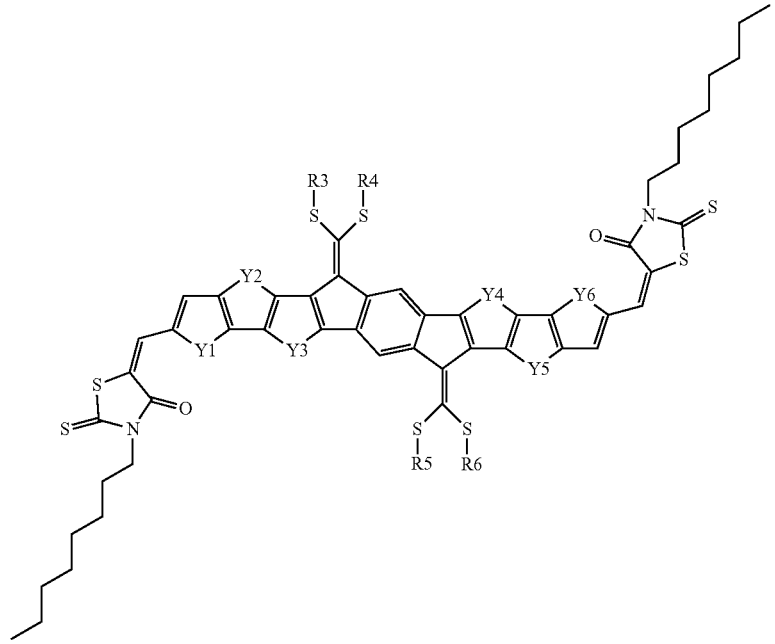
[Formula 1-20]
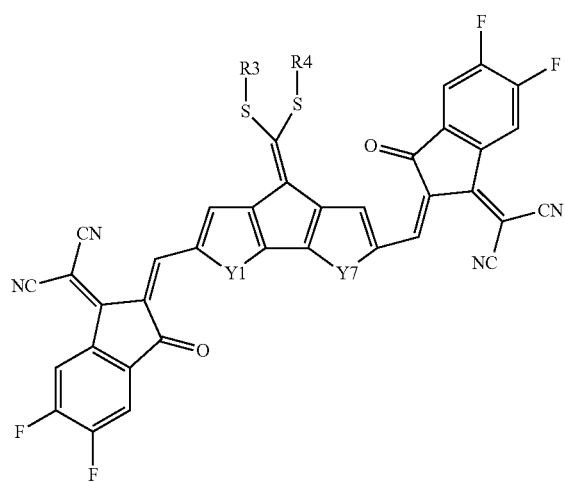
[Formula 1-21]
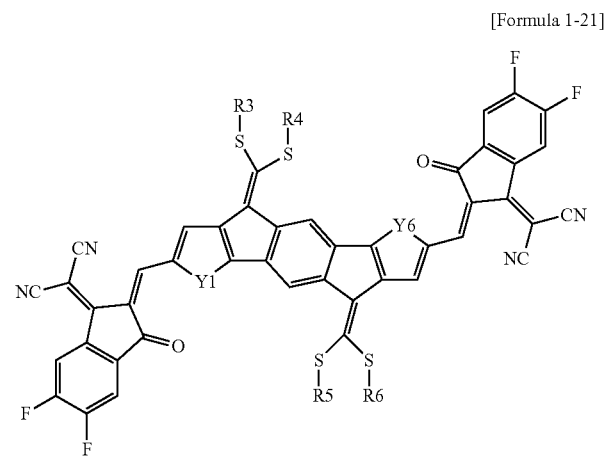
[Formula 1-22]
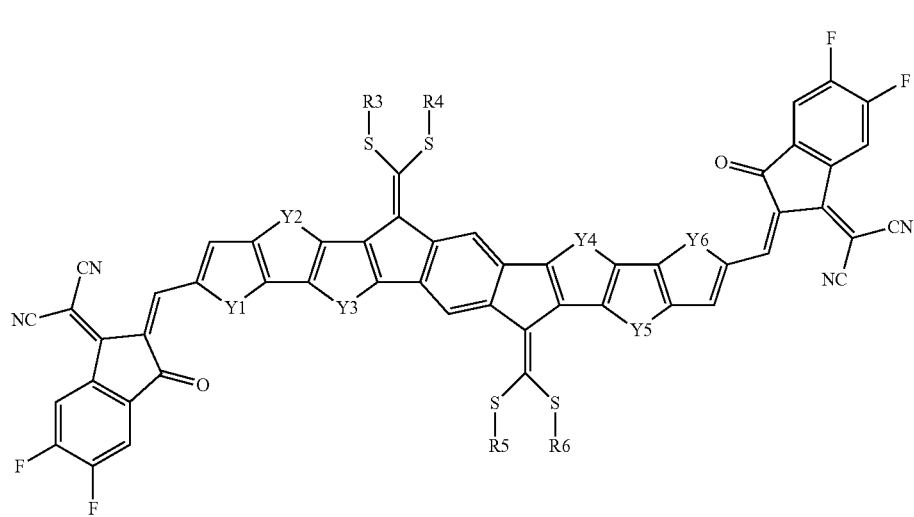

In Formulae 1-11 to 1-22,

Y1 to Y5 are the same as or different from each other, and are each independently CRR', NR, O, SiRR', PR, S, GeRR', Se, or Te, Y6 and Y7 are different from each other, and are each independently a direct bond, CRR', NR, O, SiRR', PR, S, GeRR', Se, or Te, R3 to R6, R, and R' are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In an exemplary embodiment of the present specification, Y1 to Y7 are the same as or different from each other, and are each independently CRR', NR, O, or S, and R and R' are the same as those described above.

In an exemplary embodiment of the present specification, Y1 to Y7 are the same as or different from each other, and are each independently NR or S, and R is the same as that described above.

In an exemplary embodiment of the present specification, Y1 to Y7 are each S. In an exemplary embodiment of the present specification, R3 to R6 are the same as or different from each other, and are each independently a substituted or unsubstituted alkyl group; a substituted or unsubstituted aryl group; or a substituted or unsubstituted heterocyclic group.

In an exemplary embodiment of the present specification, R3 to R6 are the same as or different from each other, and are each independently a branched alkyl group having 1 to 20 carbon atoms.

In an exemplary embodiment of the present specification, R3 to R6 are the same as or different from each other, and are each independently an alkyl group substituted with a substituted or unsubstituted heterocyclic group.

In an exemplary embodiment of the present specification, R3 to R6 are the same as or different from each other, and are each independently an alkyl group substituted with a heterocyclic group substituted with an alkyl group.

In an exemplary embodiment of the present specification, R3 to R6 are the same as or different from each other, and are each independently an alkyl group substituted with a thiophene group substituted with an alkyl group.

In an exemplary embodiment of the present specification, R3 to R6 are the same as or different from each other, and are each independently an alkyl group substituted with a thiophene group substituted with a hexyl group.

In an exemplary embodiment of the present specification, R3 to R6 are the same as or different from each other, and are each independently an alkyl group substituted with a substituted or unsubstituted aryl group.

In an exemplary embodiment of the present specification, R3 to R6 are the same as or different from each other, and are each independently an alkyl group substituted with an aryl group substituted with an alkyl group.

In an exemplary embodiment of the present specification, R3 to R6 are the same as or different from each other, and are each independently an alkyl group substituted with a phenyl group substituted with an alkyl group.

In an exemplary embodiment of the present specification, R3 to R6 are the same as or different from each other, and are each independently an alkyl group substituted with a phenyl group substituted with a hexyl group.

In an exemplary embodiment of the present specification, Formula 1 may be represented by any one of the following structures.

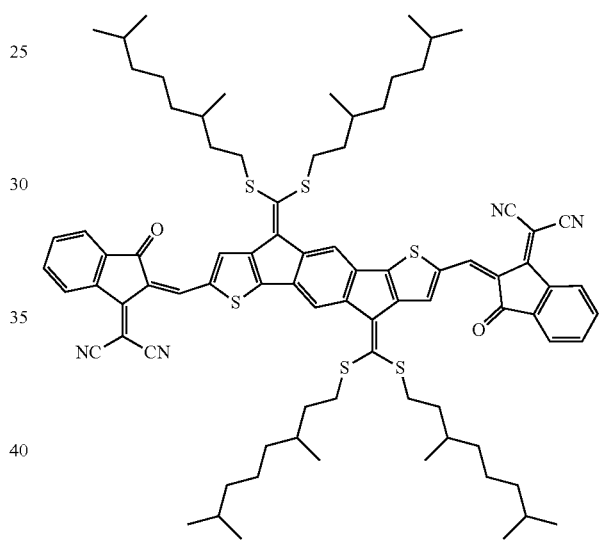

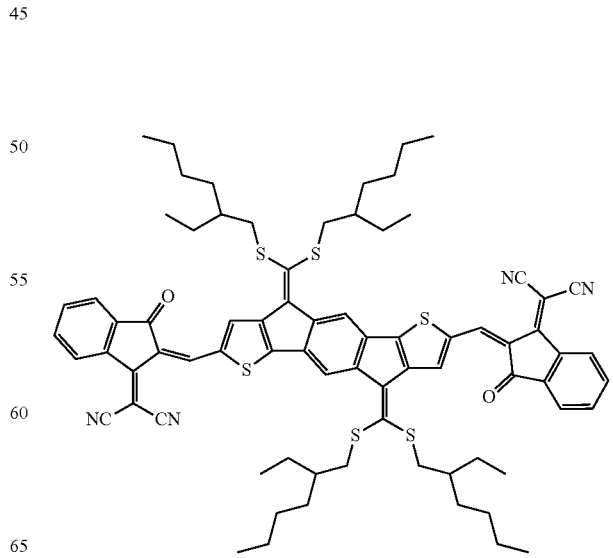

21
-continued
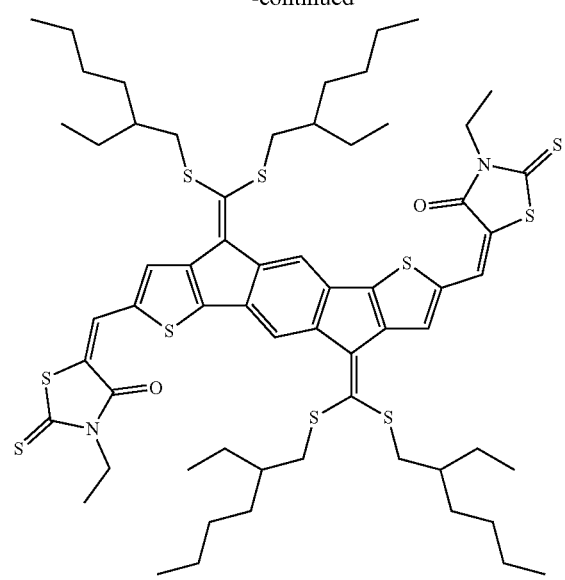
22
-continued
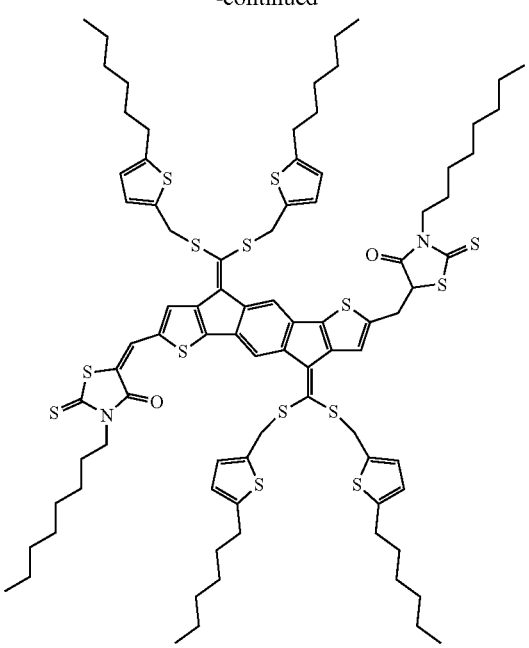
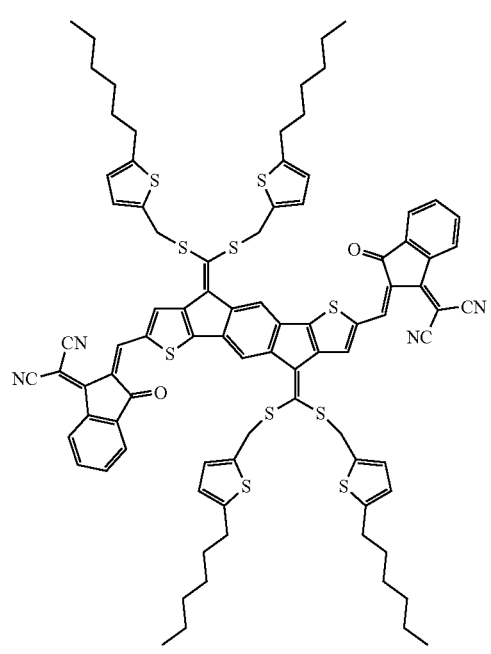
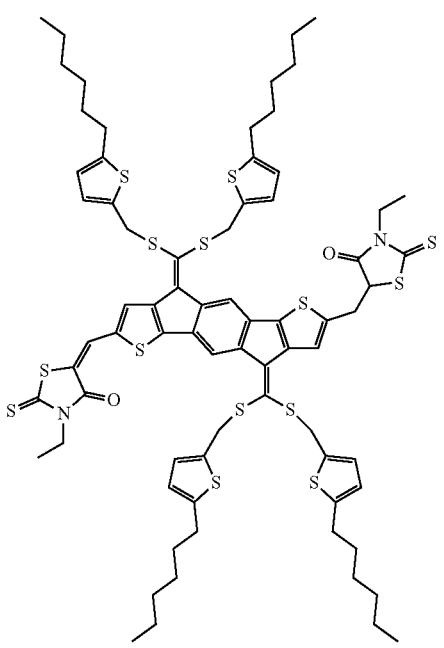

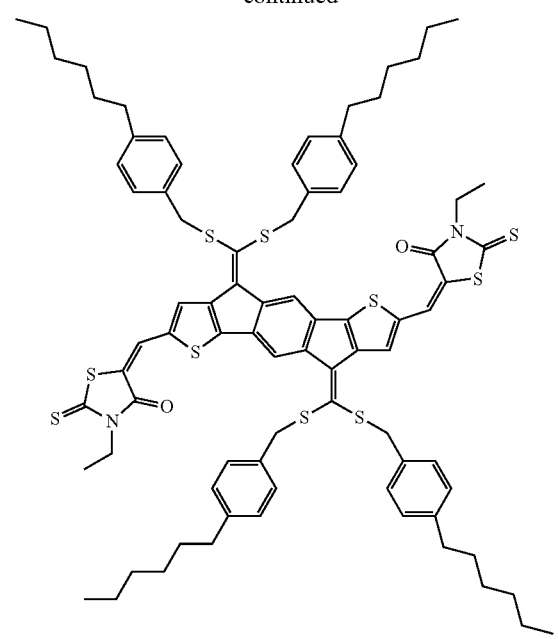
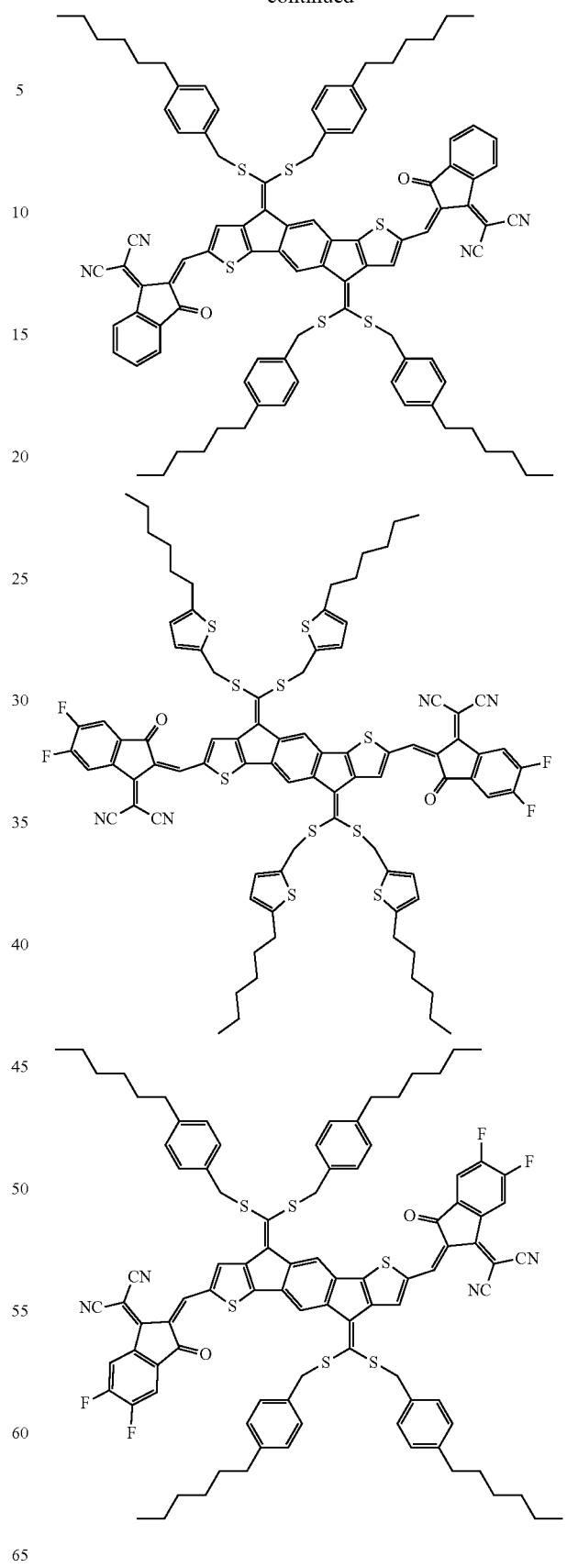

-continued

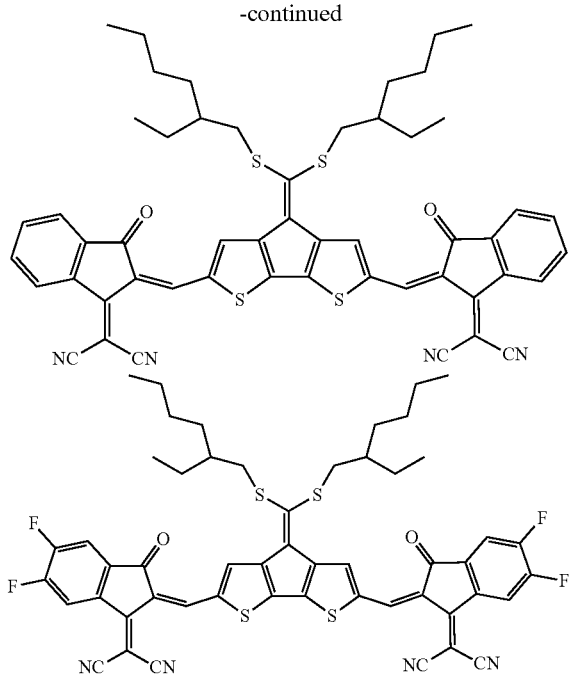

An exemplary embodiment of the present specification provides an organic solar cell including:
a first electrode;
a second electrode provided to face the first electrode; and
an organic material layer having one or more layers provided between the first electrode and the second electrode and including a photoactive layer,
in which one or more layers of the organic material layer include the compound.

In an exemplary embodiment of the present specification, the photoactive layer includes the compound.

In an exemplary embodiment of the present specification, the photoactive layer includes an electron donor material and an electron acceptor material, and the electron acceptor material includes the compound.

In an exemplary embodiment of the present specification, the electron donor and the electron acceptor may constitute a bulk heterojunction (BHJ). The electron donor material and the electron acceptor material may be mixed at a ratio (w/w) of 1:10 to 10:1. Specifically, the electron donor material and the electron acceptor material may be mixed at a ratio (w/w) of 1:1 to 1:10, and more specifically, the electron donor material and the electron acceptor material may be mixed at a ratio (w/w) of 1:1 to 1:5. If necessary, the electron donor material and the electron acceptor material may be mixed at a ratio (w/w) of 1:1 to 1:3.

In an exemplary embodiment of the present specification, a material applied in the art may be used for the electron donor, and for example, the electron donor may include one or more materials selected from the group comprising of poly 3-hexyl thiophene (P3HT), poly[N-9'-heptadecanyl-2,7-carbazole-alt-5,5-(4'-7'-di-2-thienyl-2,1',3'-benzothiadiazole)] (PCDTBT), poly[2,6-(4,4-bis-(2-ethylhexyl)-4H-cyclopenta[2,1-b']3,4-bidithiophene)-alt-4,7-(2,1,3-benzothiadiazole)] (PCPDTBT), poly[2,7-(9,9-dioctofluorene)-alt-5,5-(4,7-bis(thiophene-2-yl)benzo-2,1,3-thiadiazole)] (PFO-DBT), poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7), poly[2,7-(9,9-dioctyl-dibenzosilole)-alt-4,7-bis(thiophen-2-yl)benzo-2,1,3-thiadiazole] (PSiF-DBT), poly[4,8-bis(5-(2-ethylhexyl)thiophen-2-yl)benzo[1,2-b;4,5-b']dithiophene-2,6-diyl-alt-(4-(2-ethylhexyl)-3-fluorothieno[3,4-b]thiophene-)-2-carboxylate-2-6-diyl)](PTB7-Th), and poly(benzodithiophene-benzotriazole (PBDBT).

In an exemplary embodiment of the present specification, the photoactive layer may have a Mayer thin film structure including an n-type organic material layer and a p-type organic material layer.

In the present specification, the organic solar cell may further include an additional organic material layer. The organic solar cell may reduce the number of organic material layers by using an organic material which simultaneously has various functions.

In an exemplary embodiment of the present specification, the organic material layer includes a hole transport layer, a hole injection layer, or a layer which simultaneously transports or injects holes, and the hole transport layer, the hole injection layer, or the layer which simultaneously transports and injects holes includes the compound.

In an exemplary embodiment of the present specification, the organic material layer includes an electron transport layer, an electron injection layer, or a layer which simultaneously transports and injects electrons, and the electron transport layer, the electron injection layer, or the layer which simultaneously transports and injects electrons includes the compound.

In the present specification, when the organic solar cell accepts a photon from an external light source, an electron and a hole are generated between an electron donor and an electron acceptor. The generated hole is transported to a positive electrode through an electron donor.

In an exemplary embodiment of the present specification, an organic solar cell may be arranged in an order of a first electrode, a photoactive layer, and a second layer, and may be arranged in an order of a second electrode, a photoactive layer, and a first electrode, but the order is not limited thereto.

In an exemplary embodiment of the present specification, the organic solar cell may be arranged in an order of a first electrode, a hole transport layer, a photoactive layer, an electron transport layer, and a second layer, and may be arranged in an order of a second electrode, an electron transport layer, a photoactive layer, a hole transport layer, and a first electrode, but the order is not limited thereto.

In an exemplary embodiment of the present specification, the organic solar cell may further include a substrate.

In an exemplary embodiment of the present specification, the substrate may be a glass substrate or a transparent plastic substrate having excellent transparency, surface smoothness, ease of handling, and water proof properties, but is not limited thereto, and is not limited as long as the substrate is a substrate typically used in an organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

In an exemplary embodiment of the present specification, the organic solar cell further includes a substrate, an electron transport layer, and a hole transport layer.

FIG. 1 exemplifies the organic solar cell according to an exemplary embodiment of the present specification. Specifically, FIG. 1 exemplifies the organic solar cell according to an exemplary embodiment of the present specification, in which a first electrode 102 is provided on a substrate 101, an electron transport layer 103 is provided on the first electrode 102, a photoactive layer 104 is provided on the electron transport layer 103, a hole transport layer 105 is provided on the photoactive layer 104, and a second electrode 106 is provided on the hole transport layer 105.

In an exemplary embodiment of the present specification, the first electrode may be made of a material which is transparent and has excellent conductivity. Examples of the first electrode include: a metal such as vanadium, chromium, copper, zinc, and gold, or an alloy thereof; a metal oxide such as zinc oxide, indium oxide, indium tin oxide (ITO), and indium zinc oxide (WO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

In an exemplary embodiment of the present specification, a method of forming the first electrode is not particularly limited, but the first electrode may be formed, for example, by being applied onto one surface of a substrate or by being coated in the form of a film by using a method such as sputtering, e-beam, thermal deposition, spin coating, screen printing, inkjet printing, doctor blade, or gravure printing.

In an exemplary embodiment of the present specification, when the first electrode is formed on a substrate, the first electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a hot plate at 100 to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film may be easily formed on a first electrode, and the quality of the thin film may also be improved.

In the present specification, examples of a pre-treatment technology for a first electrode include a) a surface oxidation method using a parallel plate-type discharge, b) a method of oxidizing the surface through ozone produced by using UV (ultraviolet) rays in a vacuum state, c) an oxidation method using oxygen radicals produced by plasma, and the like.

In an exemplary embodiment of the present specification, one of the methods may be selected depending on the state of the first electrode or the substrate. However, commonly in all the methods, it is preferred to prevent oxygen from being separated from the surface of the first electrode or the substrate, and maximally inhibit moisture and organic materials from remaining. In this case, it is possible to maximize a substantial effect of the pre-treatment.

As a specific example, it is possible to use a method of oxidizing the surface through ozone produced by using UV. In this case, a patterned ITO substrate after being ultrasonically cleaned is baked on a hot plate and dried well, and then introduced into chamber, and the patterned ITO substrate may be cleaned by ozone generated by reacting an oxygen gas with UV light by operating a UV lamp.

However, the surface modification method of the patterned ITO substrate in the present specification needs not be particularly limited, and any method may be used as long as the method is a method of oxidizing a substrate.

In an exemplary embodiment of the present specification, the second electrode may be a metal having a low work function. Specific examples of the second electrode include: a metal such as magnesium, calcium, sodium, potassium, titanium, indium, yttrium, lithium, gadolinium, aluminum, silver, tin, and lead, or an alloy thereof; and a multi-layer structured material such as LiF/Al, $LiO_2$/Al, LiF/Fe, Al:Li, Al:$BaF_2$, and Al:$BaF_2$:Ba, but are not limited thereto.

In an exemplary embodiment of the present specification, the second electrode may be deposited and formed in a thermal evaporator showing a vacuum degree of $5 \times 10^{-7}$ torr or less, but the forming method is not limited to this method.

In an exemplary embodiment of the present specification, the hole transport layer and/or electron transport layer materials serve to efficiently transfer electrons and holes separated from a photoactive layer to an electrode, and the materials are not particularly limited.

In an exemplary embodiment of the present specification, the hole transport layer material may be poly(3,4-ethylenediocythiophene) doped with poly(styrenesulfonic acid) (PEDOT:PSS); molybdenum oxide ($MoO_x$); vanadium oxide ($V_2O_5$); nickel oxide (NiO); and tungsten oxide ($WO_x$), and the like, but is not limited thereto.

In an exemplary embodiment of the present specification, the electron transport layer material may be electron-extracting metal oxides, and specific examples thereof include: a metal complex of 8-hydroxyquinoline; a complex including tris(8-hydroxyquinolinato)aluminum) ($Alq_3$); a metal complex including Liq; LiF; Ca; titanium oxide ($TiO_x$); zinc oxide (ZnO); and cesium carbonate ($Cs_2CO_3$), and the like, but are not limited thereto.

In an exemplary embodiment of the present specification, the photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the forming method is not limited thereto.

MODE FOR INVENTION

In the present specification, a preparation method of the compound and the manufacture of an organic solar cell including the same will be described in detail in the following Preparation Examples and Examples. However, the following Examples are provided for exemplifying the present specification, and the scope of the present specification is not limited thereby.

Preparation Example 1

Preparation of Compound 1

(1) Preparation of Compound A-2

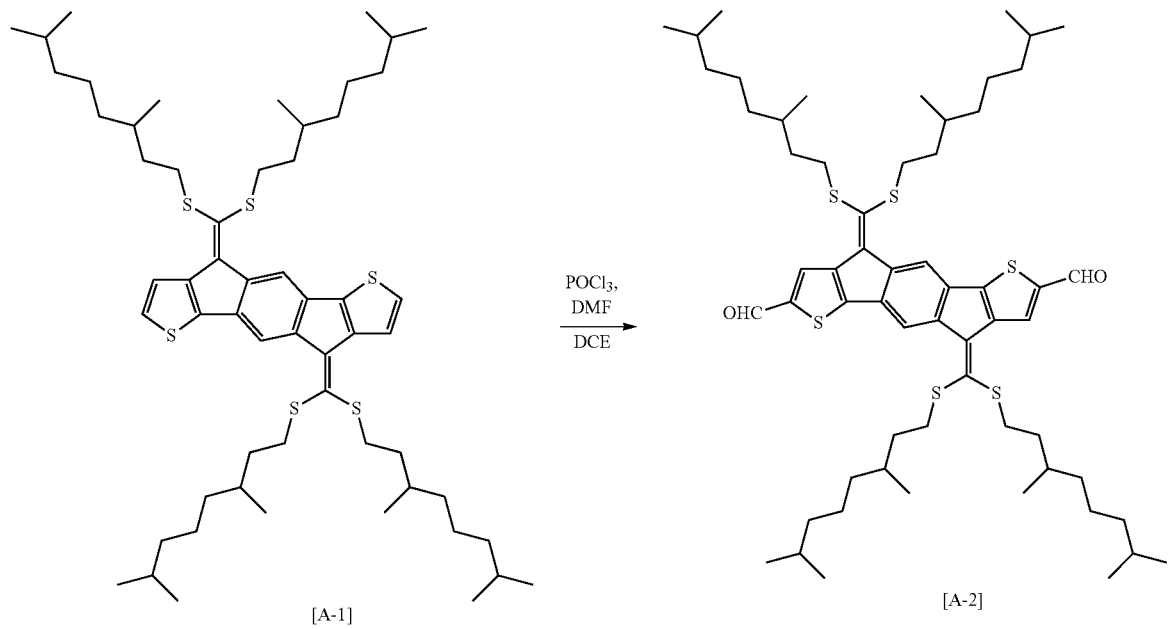

1.49 mL of phosphorus oxychloride (POCl$_3$) (16 mmol) was added to 1.55 mL of N,N-dimethylformamide (DMF) (20 mmol), and the resulting mixture was stirred at 0° C. for 60 minutes to prepare a mixed solution. A solution, in which Compound A-1 (1.53 mmol) was dissolved in 20 mL of dichloroethane (DCE), was added to the prepared mixed solution, and the resulting mixture was stirred at 100° C. for 48 hours. After the stirring, 1 M of sodium hydroxide (NaOH) was added thereto, and the resulting mixture was stirred for 1 hour for neutralization. Thereafter, the product was extracted with dichloromethane, and the extract was dried over anhydrous MgSO$_4$ and evaporated. After the solvent was removed under reduced pressure, the residue was purified through flash chromatography (hexane:chloroform=4:1) using hexane and chloroform as an eluent to obtain 1.066 g of Compound A-2. (Yield: 67.3%)

Figure 2:
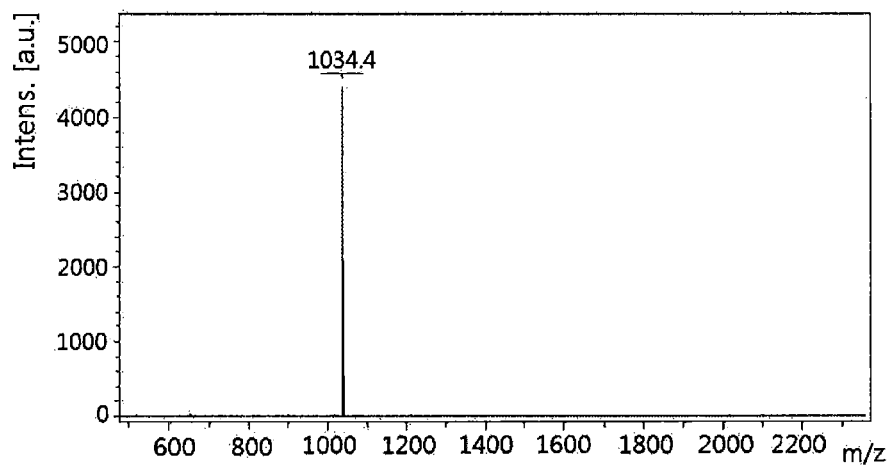
FIG. 2 is a view illustrating an MS spectrum of Compound A-2.

FIG. 2 is a view illustrating an MS spectrum of Compound A-2

(2) Preparation of Compound 1

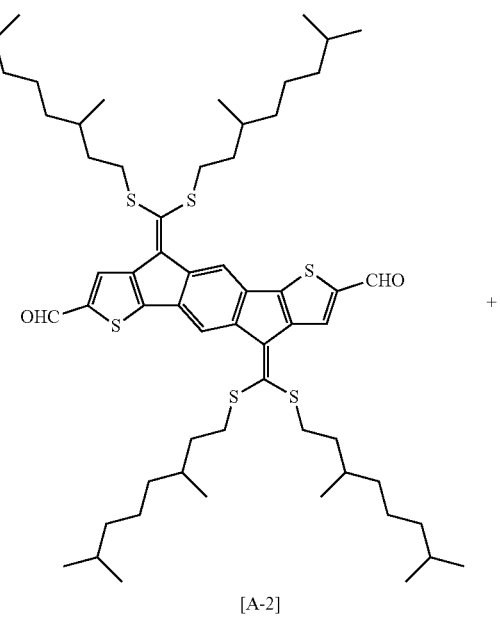

+

-continued

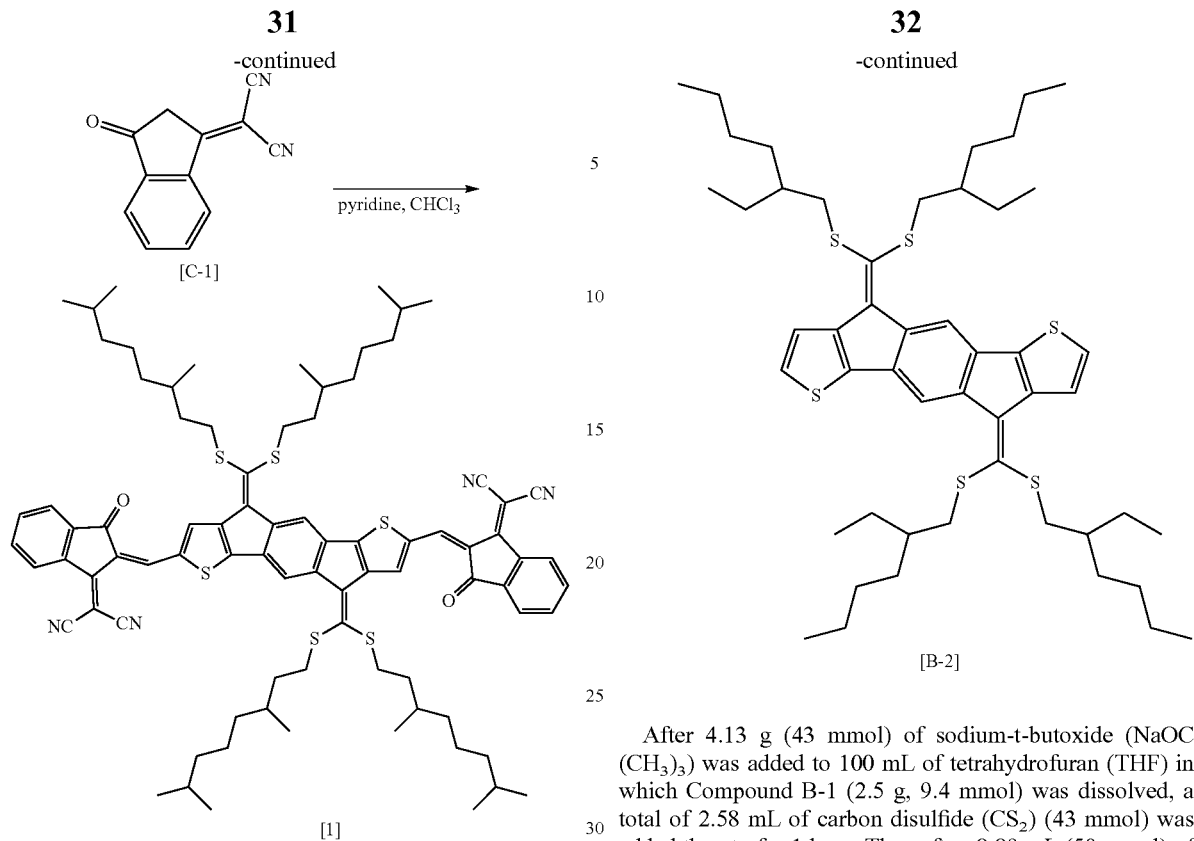

2 mL of pyridine was added to a solution in which Compound A-2 (0.725 g, 0.7 mmol) and Compound C-1 (0.68 g, 3.5 mmol) were mixed in 40 mL of chloroform (CHCl₃) under a nitrogen (N₂) atmosphere. After this mixed solution was refluxed under a nitrogen atmosphere for 24 hours, the product was extracted with dichloromethane (CH₂Cl₂), and washed with water. After the solvent was removed, the residue was recrystallized through methyl chloride (MC)/methanol, and the product was purified through chromatography using a silica gel column using hexane, acetone, ethyl acetate, and chloroform (CHCl₃) as an eluent. The produced solid was recrystallized through chloroform. Thereafter, the solid was washed with methanol and dried under a vacuum condition to obtain 905 mg of Compound 1. (Yield: 93%) (MALDI-TOF MS: 1,386.6 g/mol)

Figure 3:
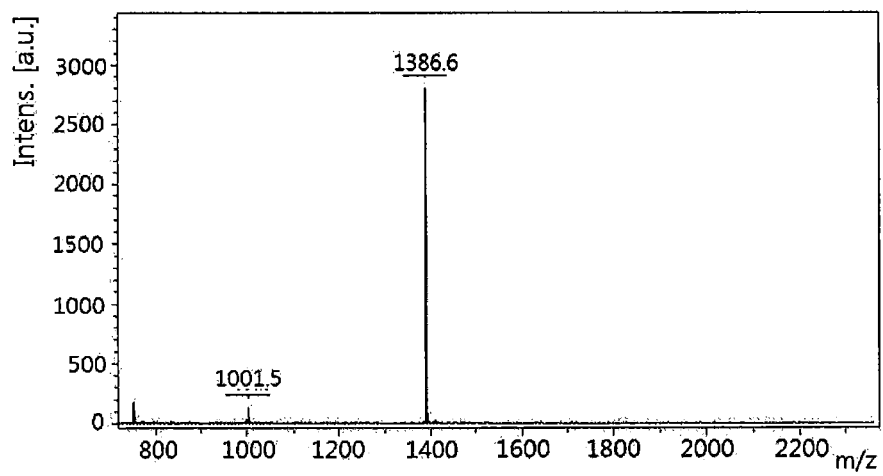
FIG. 3 is a view illustrating an MS spectrum of Compound 1.

FIG. 3 is a view illustrating an MS spectrum of Compound 1.

Preparation Example 2

Preparation of Compound 2

(1) Preparation of Compound B-2

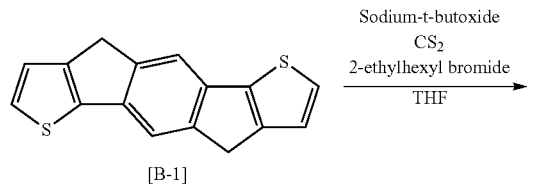

-continued

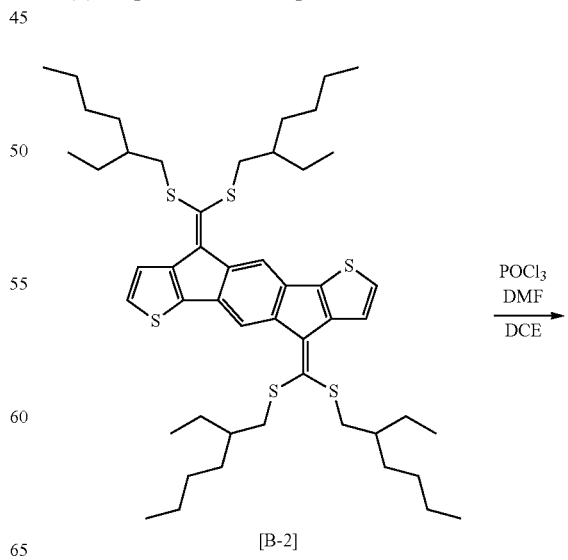

After 4.13 g (43 mmol) of sodium-t-butoxide (NaOC(CH₃)₃) was added to 100 mL of tetrahydrofuran (THF) in which Compound B-1 (2.5 g, 9.4 mmol) was dissolved, a total of 2.58 mL of carbon disulfide (CS₂) (43 mmol) was added thereto for 1 hour. Thereafter, 8.89 mL (50 mmol) of 2-ethylhexyl bromide was added thereto, and the resulting mixture was stirred for 24 hours. After the reaction, the reaction was terminated by adding ammonium hydroxide (NH₄OH) thereto, and the resulting product was extracted with dichloromethane (DCM), and then washed three times with water. The product was purified through chromatography using a silica gel column using hexane as an eluent to obtain 3.63 g of Compound B-2 in the form of a red oil. (Yield: 45%)

Figure 4:
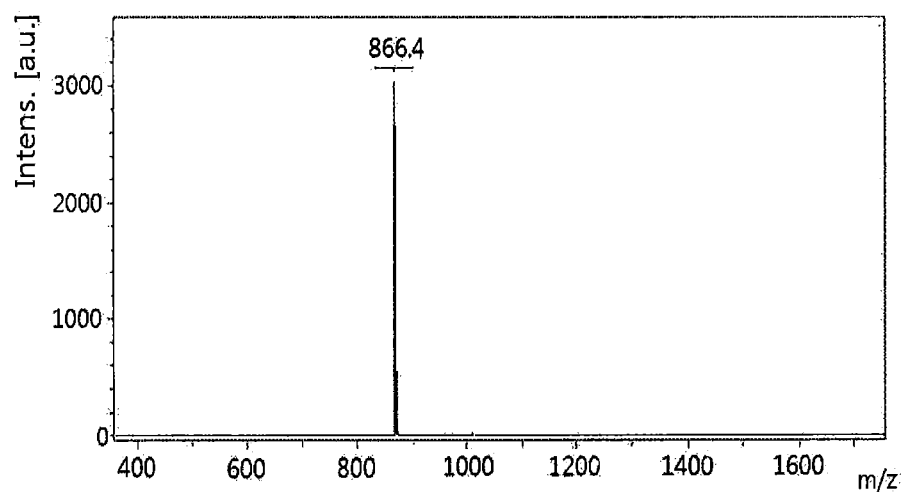
FIG. 4 is a view illustrating an MS spectrum of Compound B-2.

FIG. 4 is a view illustrating an MS spectrum of Compound B-2.

(2) Preparation of Compound B-3

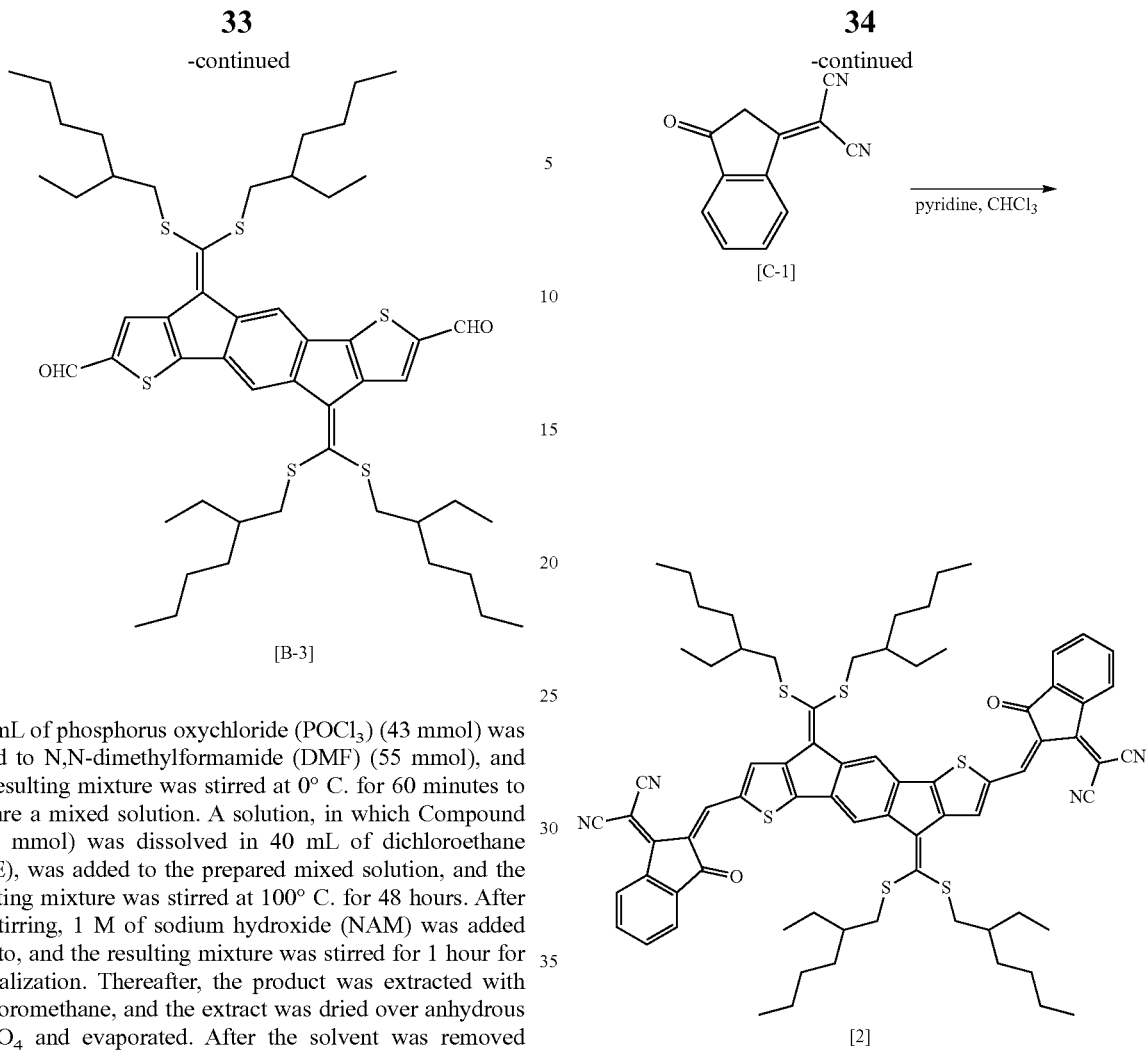

[B-3]

4 mL of phosphorus oxychloride (POCl₃) (43 mmol) was added to N,N-dimethylformamide (DMF) (55 mmol), and the resulting mixture was stirred at 0° C. for 60 minutes to prepare a mixed solution. A solution, in which Compound (4.19 mmol) was dissolved in 40 mL of dichloroethane (DCE), was added to the prepared mixed solution, and the resulting mixture was stirred at 100° C. for 48 hours. After the stirring, 1 M of sodium hydroxide (NAM) was added thereto, and the resulting mixture was stirred for 1 hour for neutralization. Thereafter, the product was extracted with dichloromethane, and the extract was dried over anhydrous MgSO₄ and evaporated. After the solvent was removed under reduced pressure, the residue was purified through flash chromatography (hexane:chloroform=4:1) using hexane and chloroform as an eluent to obtain 2.47 g of Compound B-3. (Yield: 64%)

Figure 5:
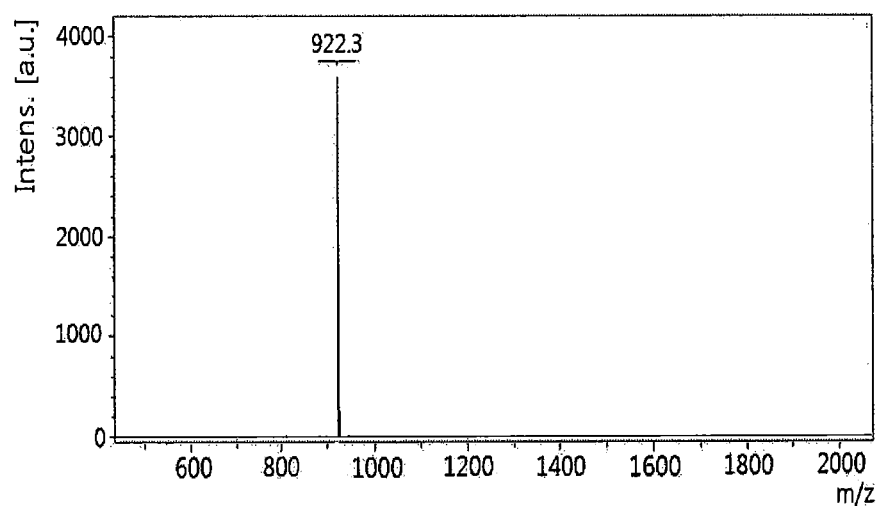
FIG. 5 is a view illustrating an MS spectrum of Compound B-3.

FIG. 5 is a view illustrating an MS spectrum of Compound B-3.

(3) Preparation of Compound 2

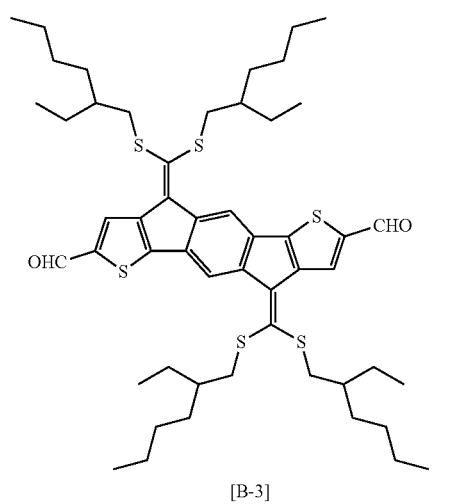

[B-3]

2 ml, of pyridine was added to a solution in which Compound B-3 (0.44 g, 0.48 mmol) and Compound C-1 (0.93 g, 4.8 mmol) were mixed in 30 of chloroform (CHCl₃) under a nitrogen (N₂) atmosphere. After this mixed solution was refluxed under a nitrogen atmosphere for 24 hours, the product was extracted with dichloromethane (CH₂Cl₂), and washed with water. After the solvent was removed, the residue was recrystallized through methyl chloride (MC)/methanol, and the product was purified through chromatography using a silica gel column using hexane, ethyl acetate, and chloroform (CHCl₃) as an eluent. The produced solid was recrystallized through chloroform. Thereafter, the product was washed with methanol and dried under a vacuum condition to obtain 550 mg of Compound 2. (Yield: 90%) (MALDI-TOF MS: 1,274.6 g/mol)

Figure 6:
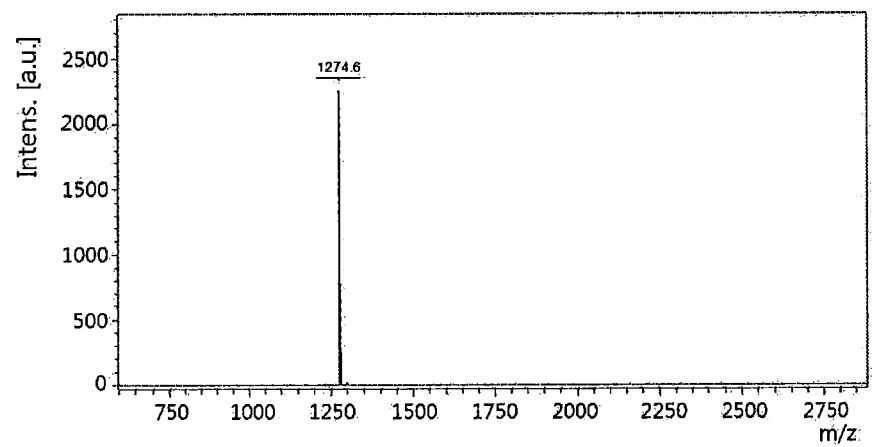
FIG. 6 is a view illustrating an MS spectrum of Compound 2.

FIG. 6 is a view illustrating an MS spectrum of Compound 2.

Preparation Example 3

Preparation of Compound 3

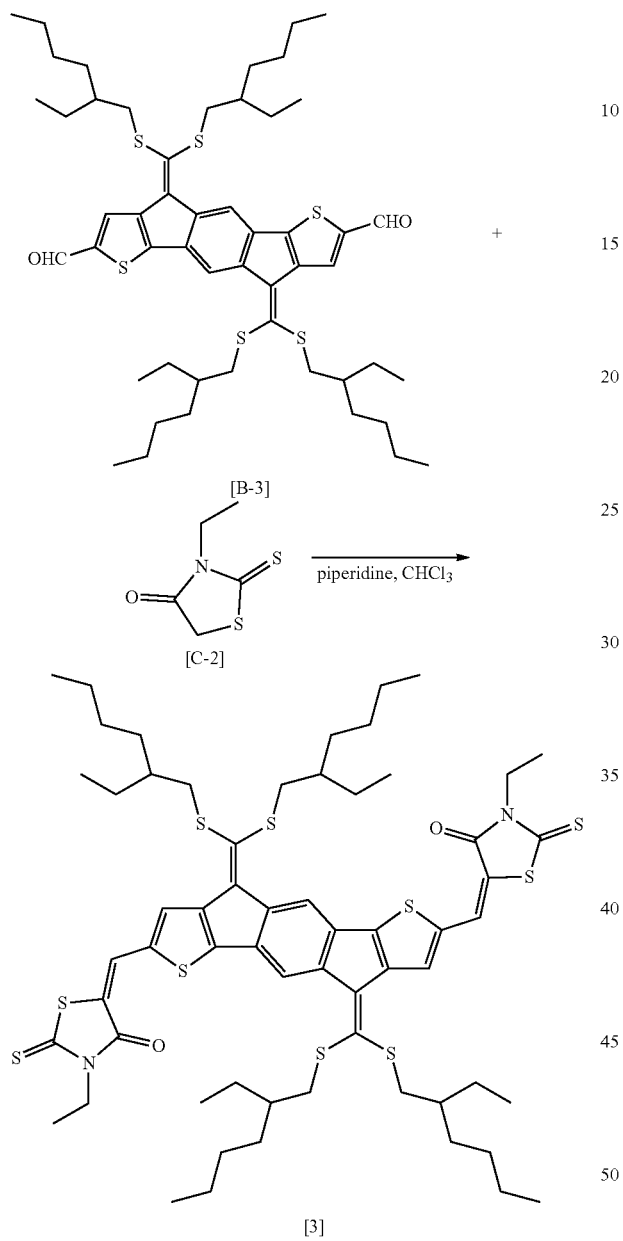

Three drops of piperidine were added to a solution in which Compound B-3 (0.83 g, 0.9 mmol) and Compound C-2 (1.45 g, 9 mmol) were mixed in 15 mL of chloroform ($CHCl_3$) under a nitrogen ($N_2$) atmosphere. After this mixed solution was refluxed under a nitrogen atmosphere for 24 hours, the product was extracted with dichloromethane ($CH_2CL_2$), and washed with water. After the solvent was removed, the residue was recrystallized through methyl chloride (MC)/methanol, and the product was purified through chromatography using a silica gel column using hexane, ethyl acetate, and chloroform ($CHCl_3$) as an eluent. The produced solid was recrystallized through chloroform. Thereafter, the product was washed with methanol and dried under a vacuum condition to obtain 918 mg of Compound 3. (Yield: 84.3%) (MALDI-TOF MS: 1,208.3 g/mol)

Figure 7:
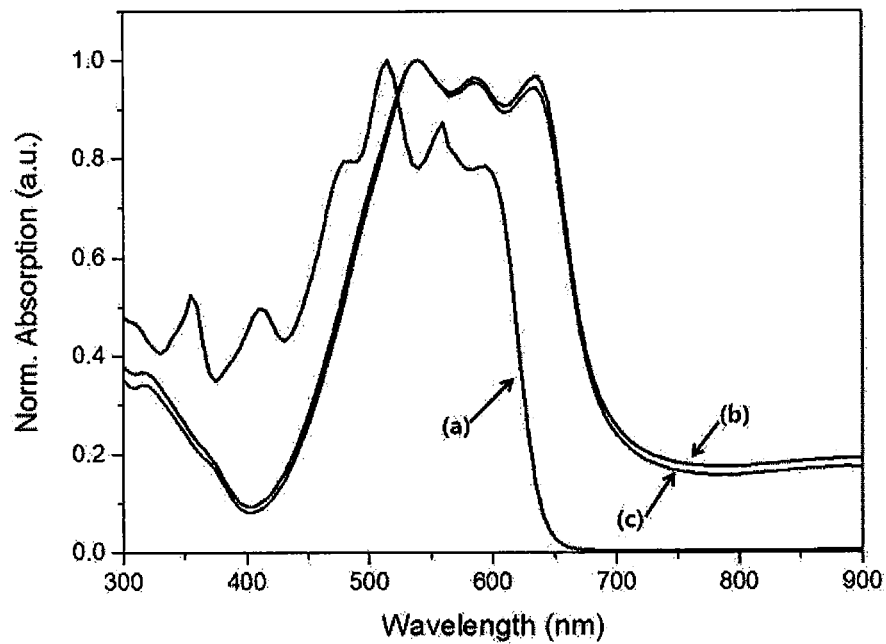
FIG. 7 is a view illustrating a UV spectrum of Compound 3.

FIG. 7 is a view illustrating UV spectrum of Compound 3.

In FIG. 7, (a) is UV data in which Compound 3 in a solution state was measured, (b) is UV data in which Compound 3 in a film state was measured, and (c) is UV data in which Compound 3 was measured after being subjected to heat treatment at 110° C. for 10 minutes in a film state.

In this case, the solution state is a state in which Compound 3 is dissolved in a chlorobenzene solution, and the film was formed from Compound 3 in a solution state by a spin-coating method.

In FIG. 7, it can be confirmed that the vibronic peak (c) after the film was subjected to heat treatment was increased as compared to the vibronic peak before the film was subjected to heat treatment. Through this, it can be confirmed that after the heat treatment, the crystallinity is excellent.

Figure 8:
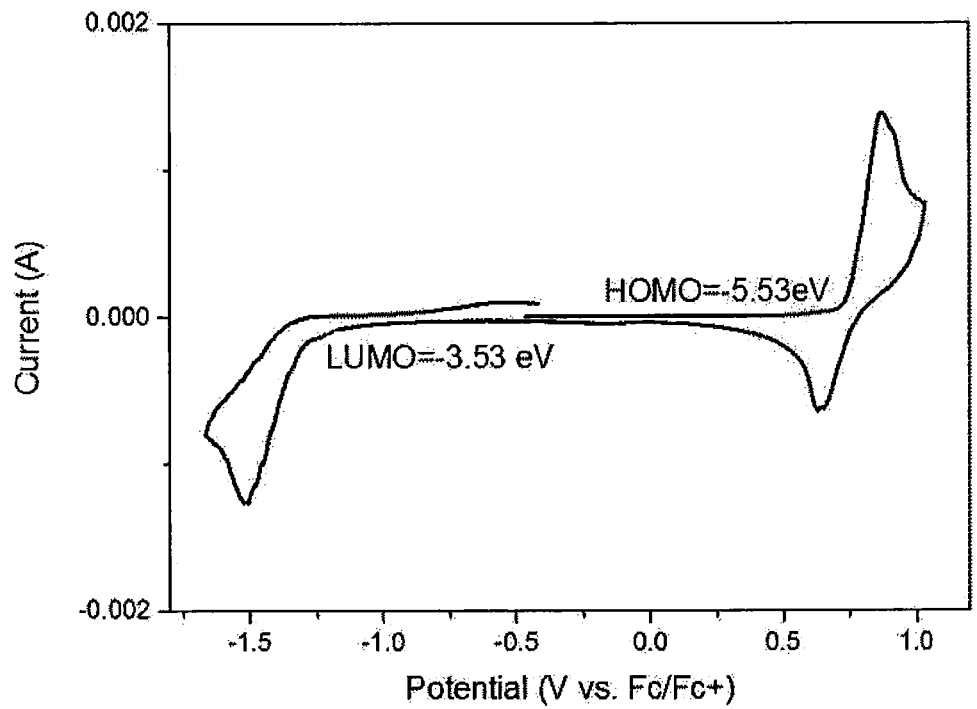
FIG. 8 is a view illustrating a measurement result of CV of Compound 3.

FIG. 8 is a view illustrating a measurement result of CV of Compound 3.

Figure 9:
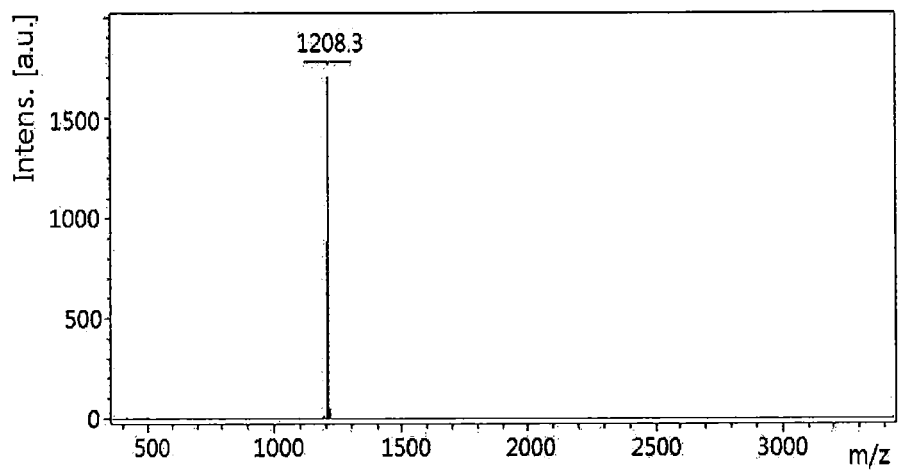
FIG. 9 is a view illustrating an MS spectrum of Compound 3.

FIG. 9 is a view illustrating an MS spectrum of Compound 3.

Preparation Example 4

Preparation of Compound 4

(1) Preparation of Compound B-4

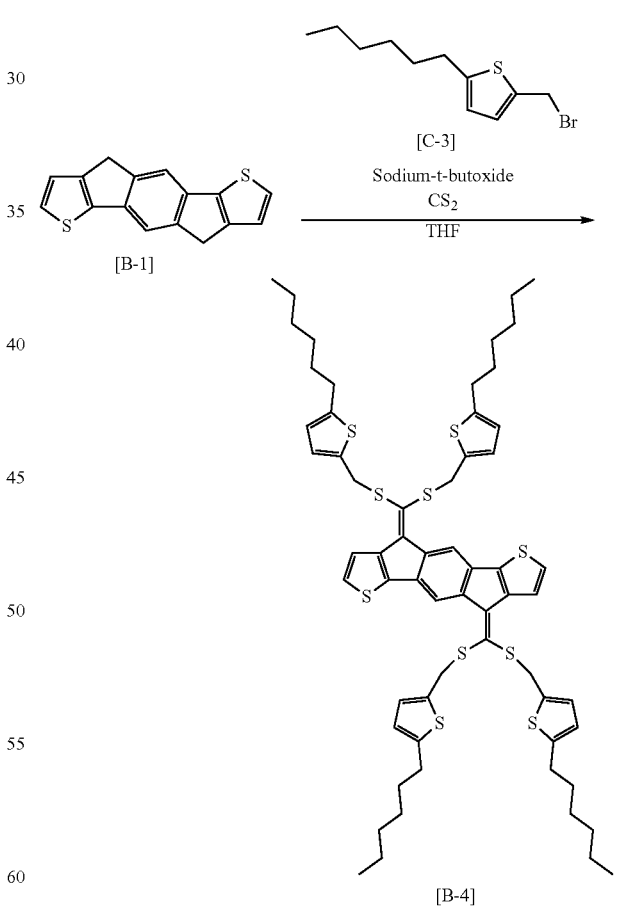

After 2.1 g (21.85 mmol) of sodium-t-butoxide (NaOC($CH_3$)$_3$) was added to a solution in which Compound B-1 (1.25 g, 4.7 mmol) was dissolved in 100 mL of tetrahydrofuran (THF) and the resulting mixture was reacted for 1 hour, 1.31 mL of carbon disulfide ($CS_2$) (21.85 mmol) was added thereto. After the reaction for 1 hour. Compound C-3 (6.53 g, 25 mmol) was added thereto, and the resulting mixture as stirred for 24 hours. After the reaction, the reaction was terminated by adding ammonium hydroxide (NH$_4$OH) thereto, and the resulting product was extracted with dichloromethane (DCM), and then washed three times with water. The product was purified through chromatography using a silica gel column using hexane as an eluent to obtain 2.15 g of Compound B-4 in the form of a red viscous oil. (Yield: 40%) (LCQ MS: 1,140.1 g/mol)

(2) Preparation of Compound B-5

4 mL, of phosphorus oxychloride POCl$_3$) (43 mmol) was added to N,N-dimethylformamide (DMF) (55 mmol), and the resulting mixture was stirred at 0° C. for 60 minutes to prepare a mixed solution. A solution, in which Compound B-4 (4.77 g, 4.19 mmol) was dissolved in 40 mL of dichloroethane (DCE), was added to the prepared mixed solution, and the resulting mixture was stirred at 100° C. for 48 hours. After the stirring, 1 M of sodium hydroxide (NaOH) was added thereto, and the resulting mixture was stirred for 1 hour for neutralization. Thereafter, the product was extracted with dichloromethane, and the extract was dried over anhydrous MgSO$_4$ and evaporated. After the solvent was removed under reduced pressure, the residue was purified through flash chromatography (hexane:chloroform=4:1) using hexane and chloroform as an eluent to obtain 4.1 g of Compound B-5. (Yield: 8 (MALDI-TOF MS: 1,196.2 g/mol)

(3) Preparation of Compound 4

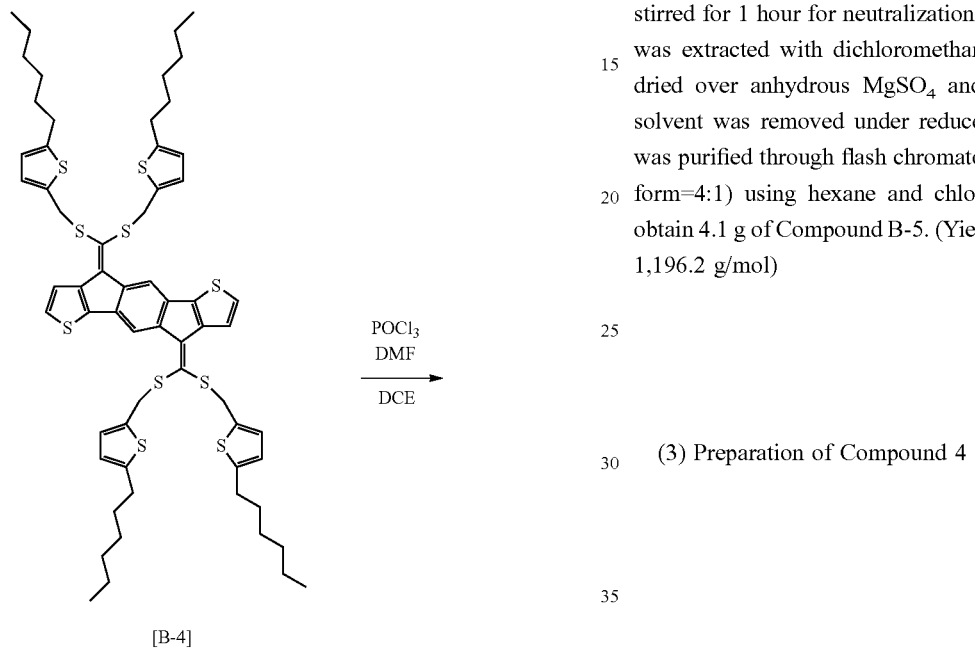

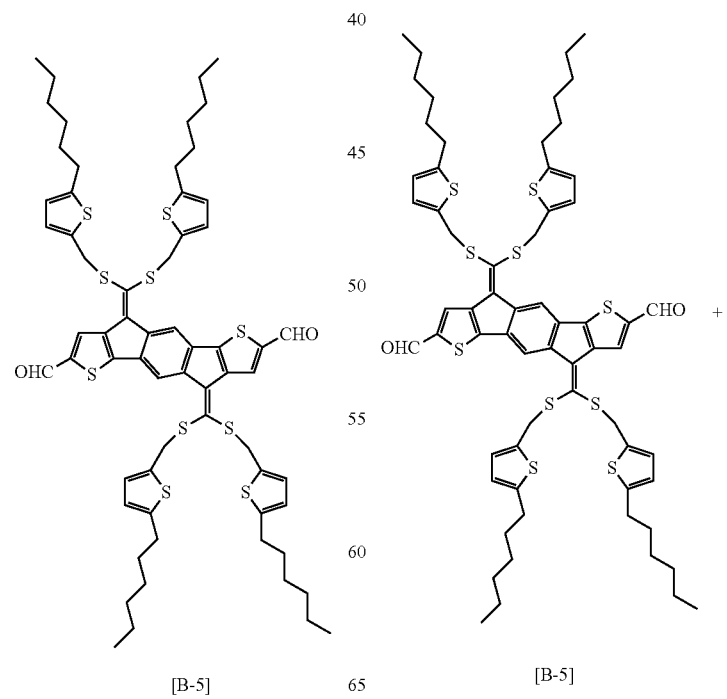

-continued

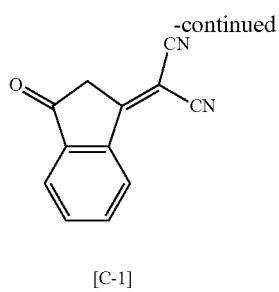

[C-1]

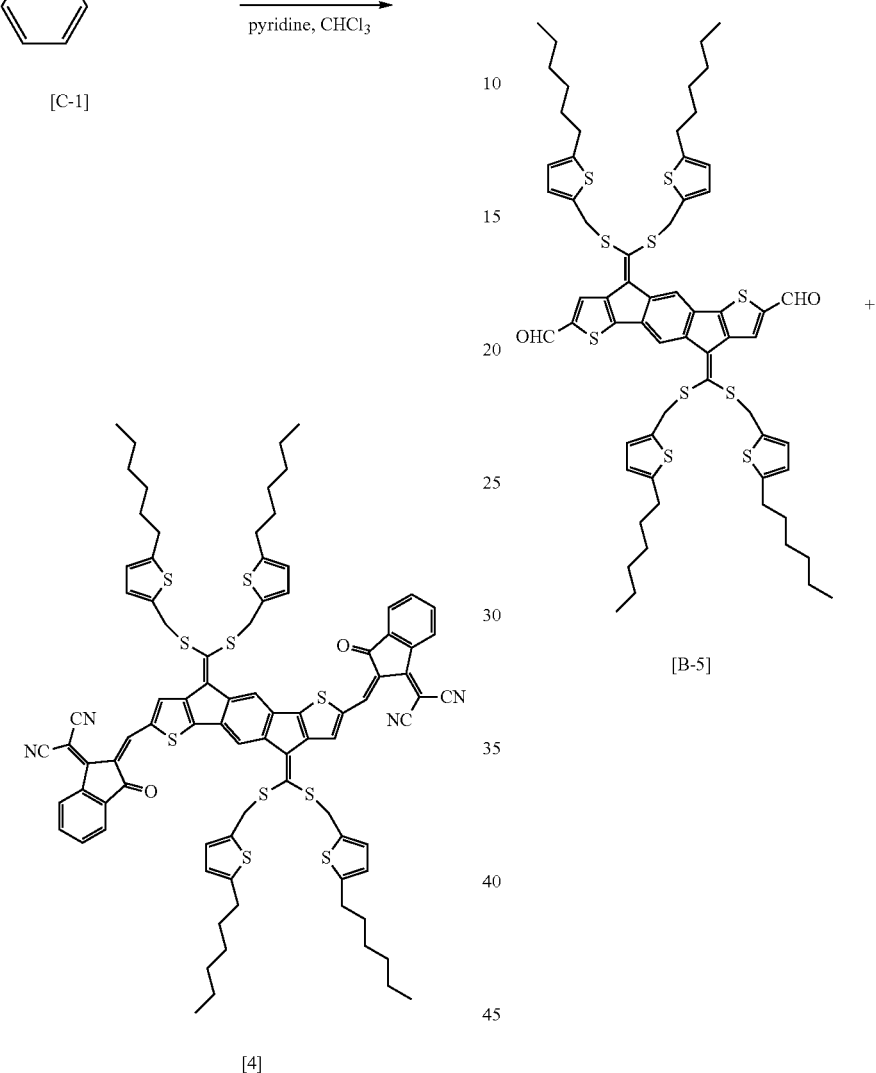

[4]

Preparation Example 5

Preparation of Compound 5

[B-5]

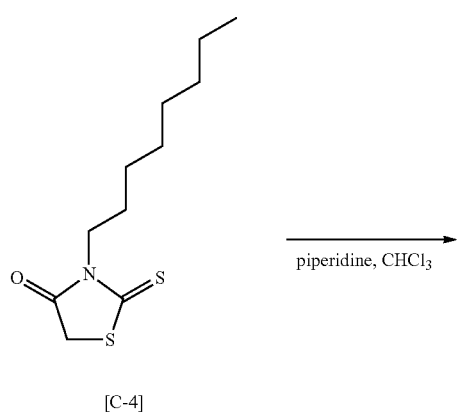

[C-4]

2 mL of pyridine was added to a solution in which Compound B-5 (1 g, 0.84 mmol) and Compound C-1 (1.55 g, 8 mmol) were mixed in 30 mL of chloroform ($CHCl_3$) under a nitrogen ($N_2$) atmosphere. After this mixed solution was refluxed under a nitrogen atmosphere for 24 hours, the product was extracted with dichloromethane ($CH_2Cl_2$), and washed with water. After the solvent was removed, the residue was recrystallized through methyl chloride (MC)/methanol, and the product was purified through chromatography using a silica gel column using hexane, ethyl acetate, and chloroform ($CHCl_3$) as an eluent. The produced solid was recrystallized through chloroform. Thereafter, the product was washed with methanol and dried under a vacuum condition to obtain 950 mg of Compound 4. (Yield: 73%) (MALDI-TOF MS: 1,548.2 g/mol)

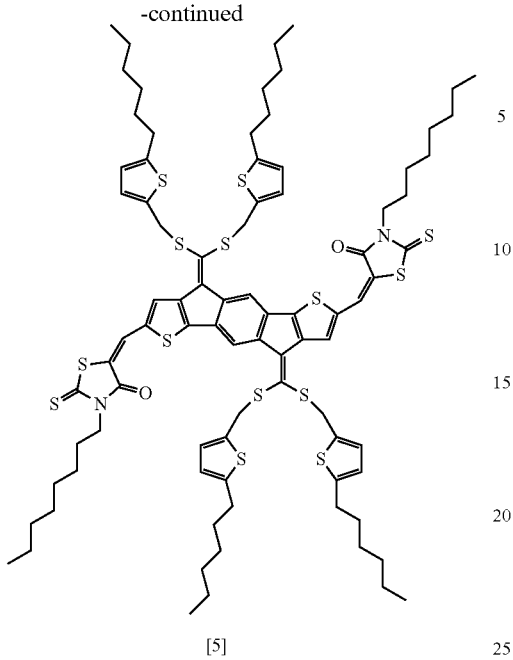

[5]

Three drops of piperidine were added to a solution in which Compound B-5 (1 g, 0.84 mmol) and Compound C-4 (1.96 g, 8 mmol) were mixed in 30 mL of chloroform (CHCl$_3$) under a nitrogen (N$_2$) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform. Thereafter, the product was washed with methanol and dried under a vacuum condition to obtain 1.04 g of Compound 5. (Yield: 75%) (MALDI-TOF MS: 1,650.6 g/mol)

Preparation Example 6

Preparation of Compound 6

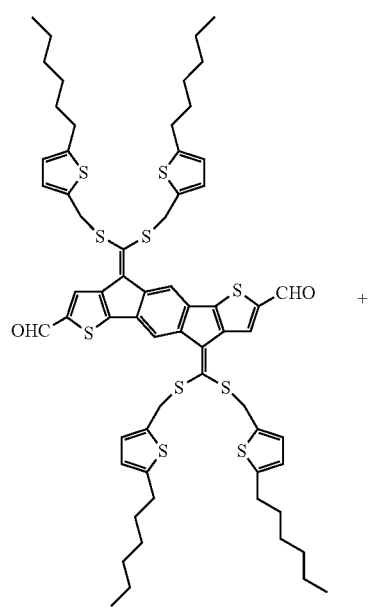

[B-5]

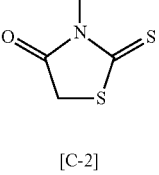

[C-2]

piperidine, CHCl$_3$

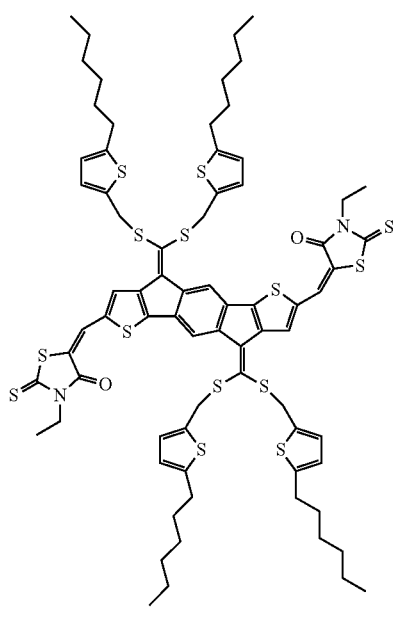

[6]

Three drops of piperidine were added to a solution in which Compound B-5 (1 g, 0.84 mmol) and Compound C-2 (1.29 g, 8 mmol) were mixed in 30 mL of chloroform (CHCl$_3$) under a nitrogen (N$_2$) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform.

Thereafter, the product was washed with methanol and dried under a vacuum condition to obtain 860 mg of Compound 6. (Yield: 69%) (MALDI-TOF MS: 1,482.2 g/mol)

Preparation Example 7

Preparation of Compound 7

(1) Preparation of Compound B-6

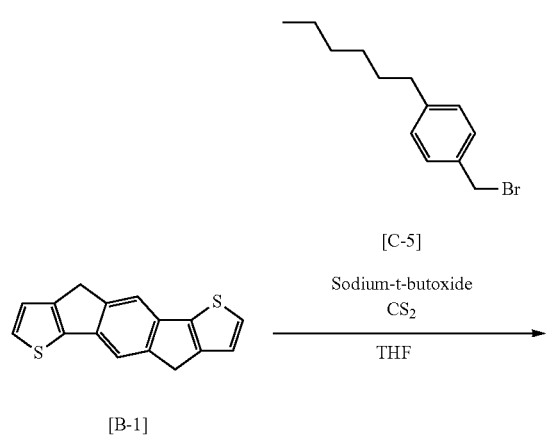

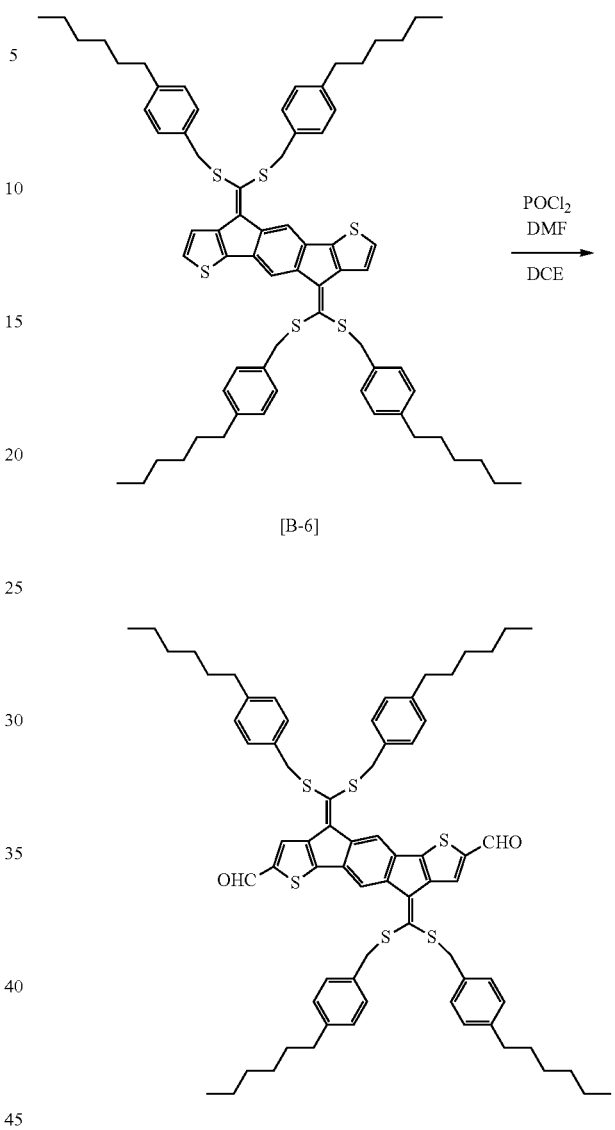

After 2.1 g (21.85 mmol) of sodium-t-butoxide (NaOC(CH$_3$)$_3$) was added to a solution in which Compound B-1 (1.25 g, 4.7 mmol) was dissolved in 100 mL of tetrahydrofuran (THF), the resulting mixture was reacted for 1 hour. After the reaction, 1.31 mL of carbon disulfide (CS$_2$) (21.85 mmol) was added thereto, and the resulting mixture was reacted for 1 hour. Thereafter, Compound C-5 (6.38 g, 25 mmol) was added thereto, and the resulting mixture was stirred for 24 hours. After the reaction, the reaction was terminated by adding ammonium hydroxide (Na$_4$OH) thereto, and the resulting product was extracted with dichloromethane (DCM), and then washed three times with water. The product was purified through chromatography using a silica gel column using hexane as an eluent to obtain 2.5 g of Compound B-6 in the form of a red viscous oil. (Yield: 48%) (LCQ MS: 1,115.3 g/mol)

(2) Preparation of Compound 13-7

4 mL of phosphorus oxychloride (POCl$_3$) (4 mmol) was added to N,N-dimethylformamide (DMF) (55 mmol), and the resulting mixture was stirred at 0° C. for 60 minutes to prepare a mixed solution. A solution, in which Compound B-6 (4.67 g, 4.19 mmol) was dissolved in 40 mL of dichloroethane (DCE), was added to the prepared mixed solution, and the resulting mixture was stirred at 100° C. for 48 hours. After the stirring, 1 M of sodium hydroxide (NaOH) was added thereto, and the resulting mixture was stirred for 1 hour for neutralization. Thereafter, the product was extracted with dichloromethane, and the extract was dried over anhydrous MgSO$_4$ and evaporated. After the solvent was removed under reduced pressure, the residue was purified through flash chromatography (hexane:chloroform=4:1) using hexane and chloroform as an eluent to obtain 3.5 g of Compound B-7. (Yield: 71%) (MALDI-TOF MS: 1,171.5 g/mol)

Figure 10:
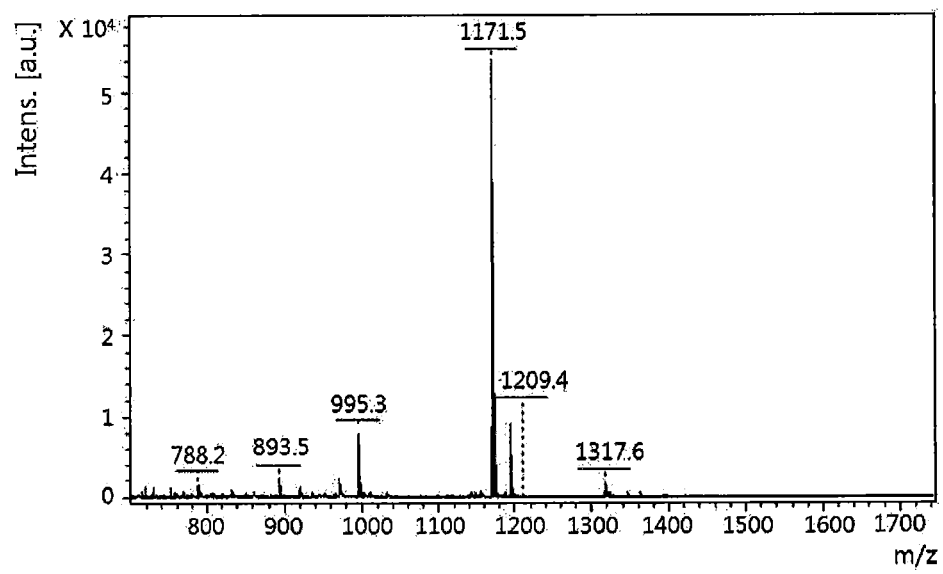
FIG. 10 is a view illustrating a measurement result of MALDI-TOF of Compound B-7.

FIG. 10 is a view illustrating a measurement result of MALDI-TOF of Compound B-7.

(3) Preparation of Compound 7

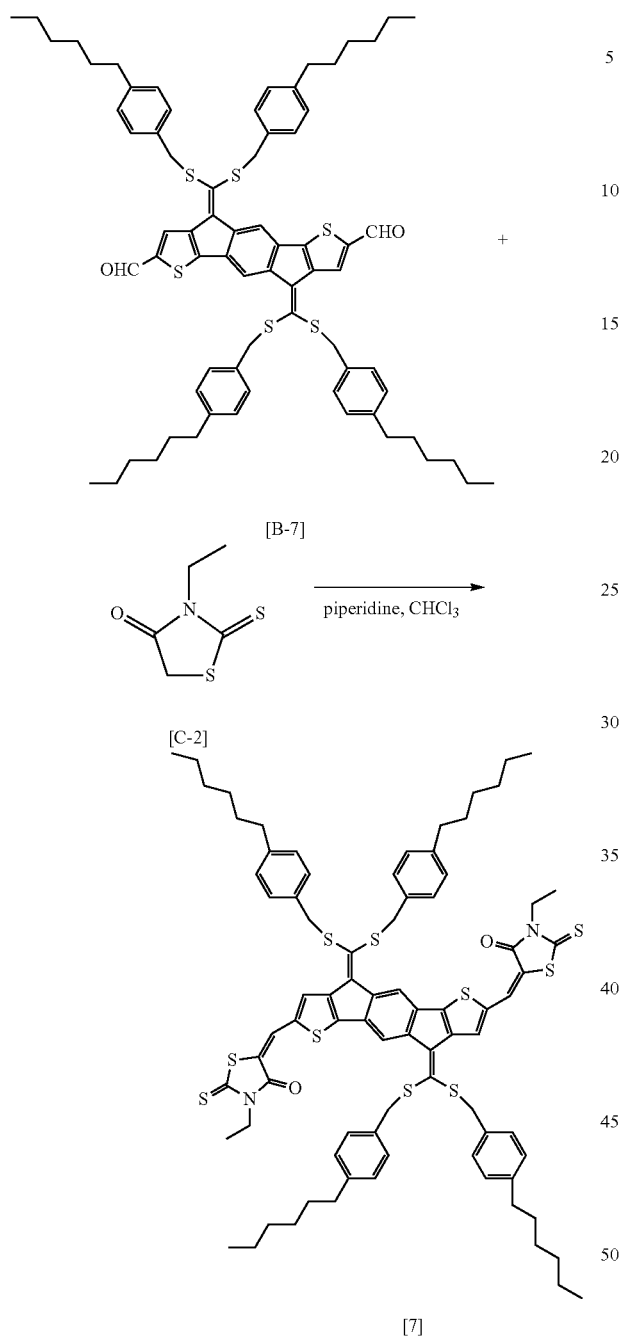

Three drops of piperidine were added to a solution in which Compound B-7 (1 g, 0.85 mmol) and Compound C-2 (1.29 g, 8 mmol) were mixed in 30 mL of chloroform (CHCl$_3$) under a nitrogen (N$_2$) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform. Thereafter, the product was washed with methanol and dried under a vacuum condition to obtain 970 mg of Compound 7. (Yield: 78%) (MALDI-TOF MS: 1,457.6 g/mol)

Preparation Example 8

Preparation of Compound 8

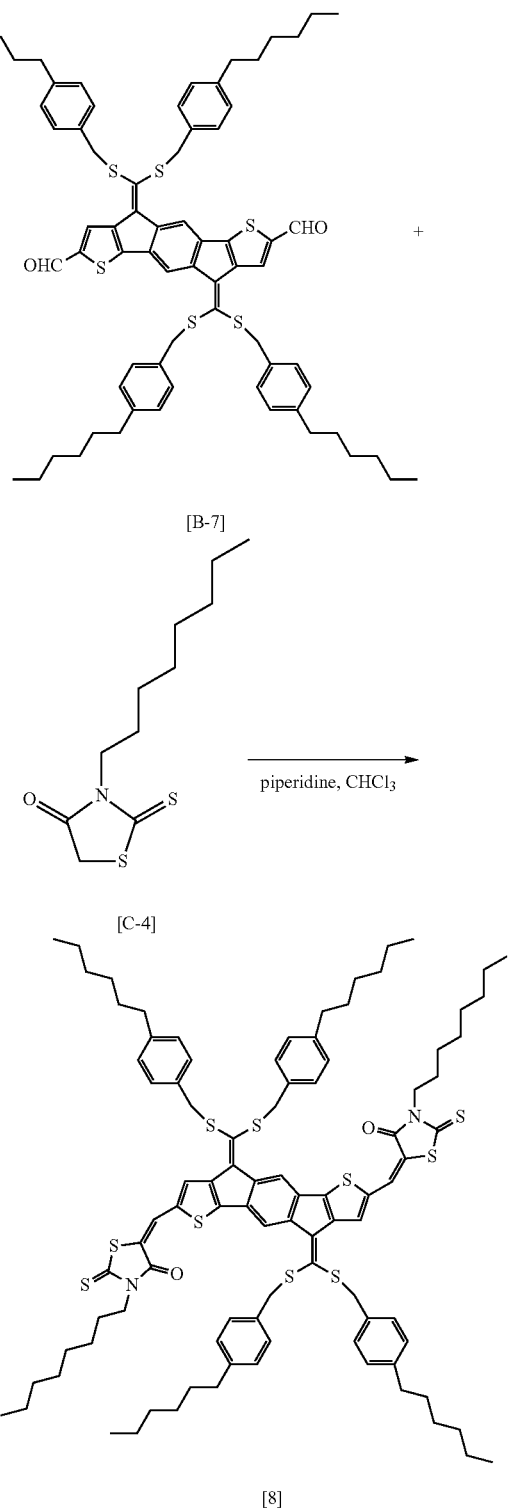

Three drops of piperidine were added to a solution in which Compound B-7 (1 g, 0.85 mmol) and Compound C-4 (1.96 g, 8 mmol) were mixed in 30 mL of chloroform (CHCl$_3$) under a nitrogen (N$_2$) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform. Thereafter, the product was washed with methanol and dried under a vacuum condition to obtain 1.1 g of Compound 8. (Yield: 80%) (MALDI-TOF MS: 1,627.1 g/mol)

Preparation Example 9

Preparation of Compound 9

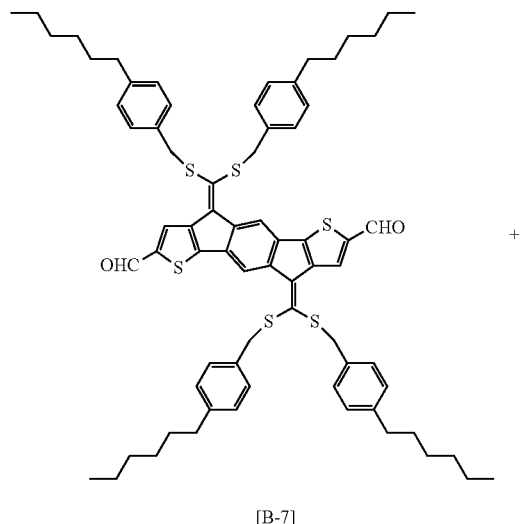

[B-7]

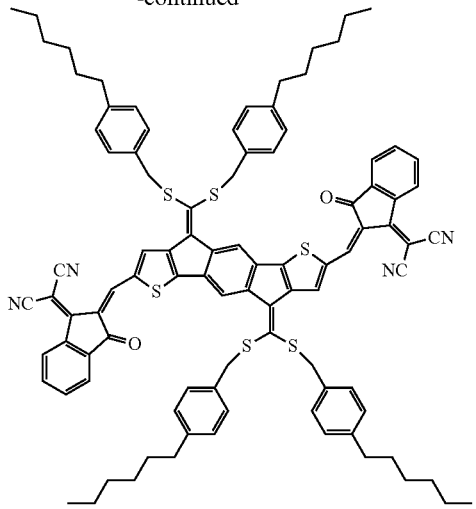

[9]

2 mL of pyridine was added to a solution in which Compound B-7 (1 g, 0.85 mmol) and Compound C-1 (1.55 g, 8 mmol) were mixed in 30 mL of chloroform (CHCl$_3$) under a nitrogen (N$_2$) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform. Thereafter, the product was washed with methanol and dried under a vacuum condition to obtain 910 mg of Compound 9. (Yield: 70%) (MALDI-TOF MS: 1,524.1 g/mol)

Preparation Example 10

Preparation of Compound 10

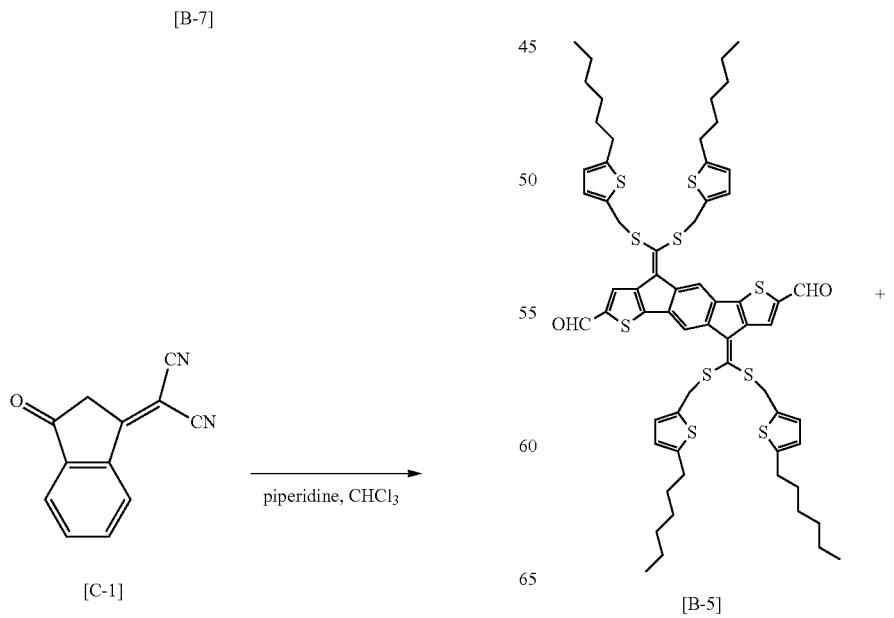

[C-1]   [B-5]

-continued

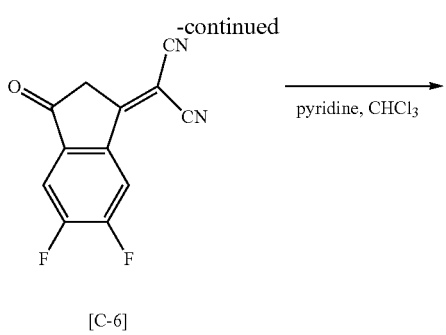

[C-6]

Preparation Example 11

Preparation of Compound 11

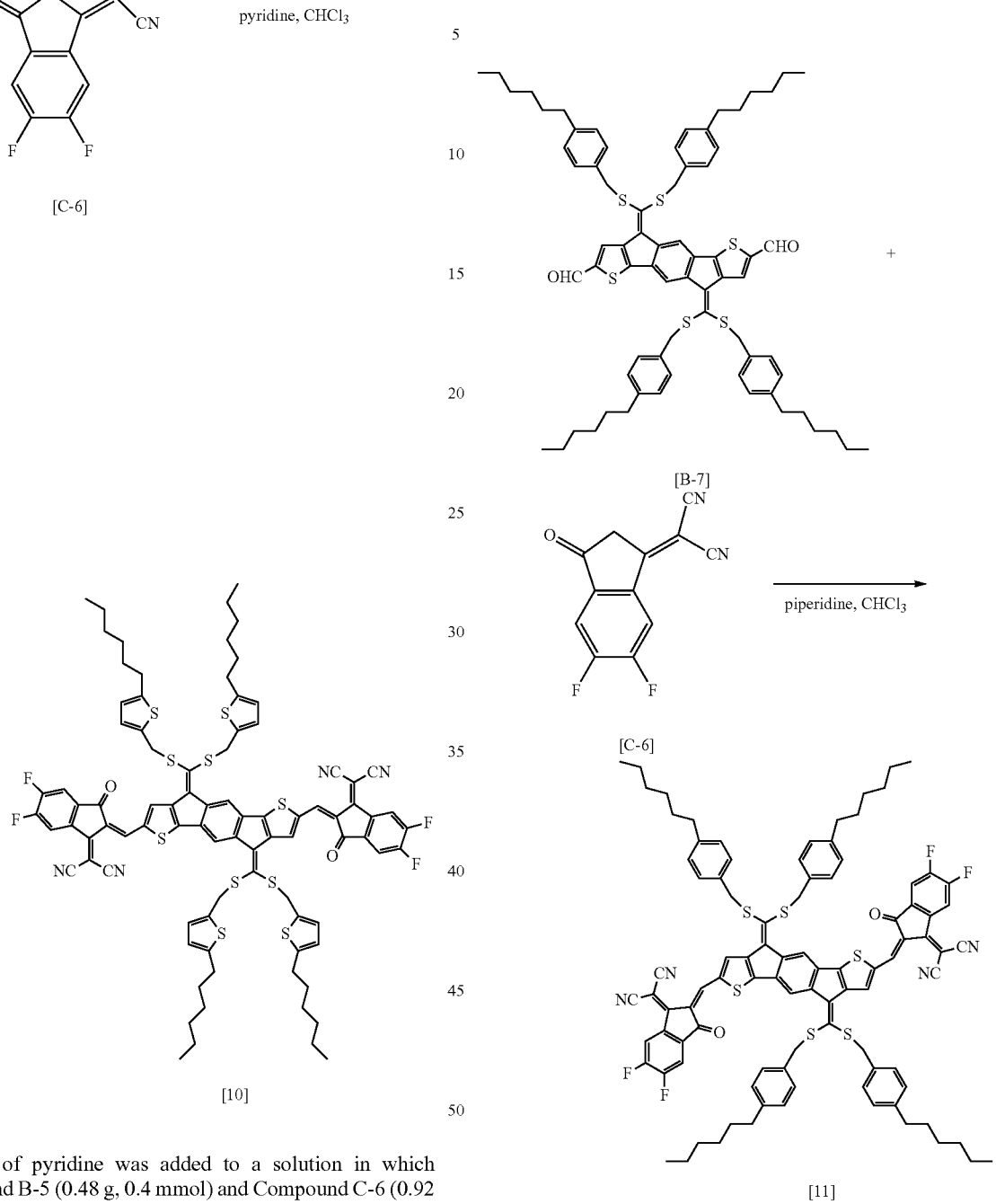

2 mL of pyridine was added to a solution in which Compound B-5 (0.48 g, 0.4 mmol) and Compound C-6 (0.92 g, 4 mmol) were mixed in 30 mL of chloroform ($CHCl_3$) under a nitrogen ($N_2$) atmosphere. After this mixed solution was refluxed under a nitrogen atmosphere for 4 hours, the product was extracted with dichloromethane ($CH_2Cl_2$), and washed with water. After the solvent was removed, the residue was recrystallized through methyl chloride (MC)/methanol, and the product was purified through chromatography using a silica gel column using hexane, ethyl acetate, and chloroform ($CHCl_3$) as an eluent. The produced solid was recrystallized through chloroform. Thereafter, the product was washed with methanol and dried under a vacuum condition to obtain 410 mg of Compound 10. (Yield: 64%) (MALDI-TOF MS: 1,618.5 g/mol)

2 mL of pyridine was added to a solution in which Compound B-7 (0.5 g, 0.43 mmol) and Compound C-6 (0.99 g, 4.3 mmol) were mixed in 30 mL of chloroform ($CHCl_3$) under a nitrogen ($N_2$) atmosphere. After this mixed solution was refluxed under a nitrogen atmosphere for 24 hours, the product was extracted with dichloromethane ($CH_2Cl_2$), and washed with water. After the solvent was removed, the residue was recrystallized through methyl chloride (MC)/methanol, and the product was purified through chromatography using a silica gel column using hexane, ethyl acetate, and chloroform (CHCl3) as an eluent. The produced solid was recrystallized through chloroform. Thereafter, the product was washed with methanol and dried under a vacuum condition to obtain 492 mg of Compound 11. (Yield: 72%) (MALDI-TOF MS: 1,594.4 g/mol)

Preparation Example 12

Preparation of Compound 12

(1) Preparation of Compound D-2

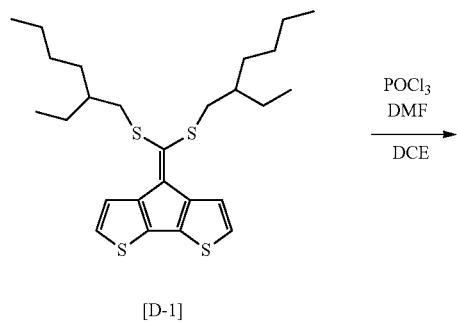

[D-1]

[D-2]

0.56 mL of phosphorus oxychloride (POCl$_3$) (6 mmol) was added to N,N-dimethylformamide (DMF) (0.54 mL, 7 mmol), and the resulting mixture was stirred at 0° C. for 60 minutes to prepare a mixed solution. A solution, in which Compound D-1 (1.20 g, 2.51 mmol) was dissolved in 20 mL of dichloroethane (DCE), was added to the prepared mixed solution, and the resulting mixture was stirred at 100° C. for 48 hours, After the stirring, 1 M of sodium hydroxide (NaOH) was added thereto, and the resulting mixture was stirred for 1 hour for neutralization. Thereafter, the product was extracted with dichloromethane, and the extract was dried over anhydrous MgSO$_4$ and evaporated. After the solvent was removed under reduced pressure, the residue was purified through flash chromatography (hexane:chloroform=4:1) using hexane and chloroform as an eluent to obtain 0.86 g of Compound D-2. (Yield: 64%) (MALDI-TOF MS: 534.2 g/mol)

(2) Preparation of Compound 12

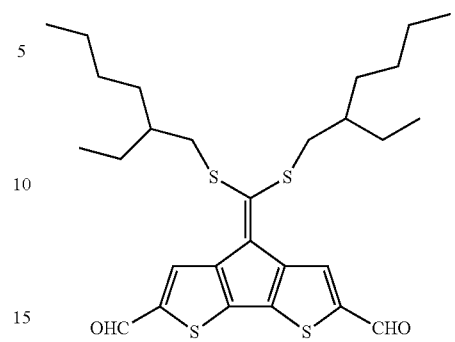

[D-2]

[C-1]

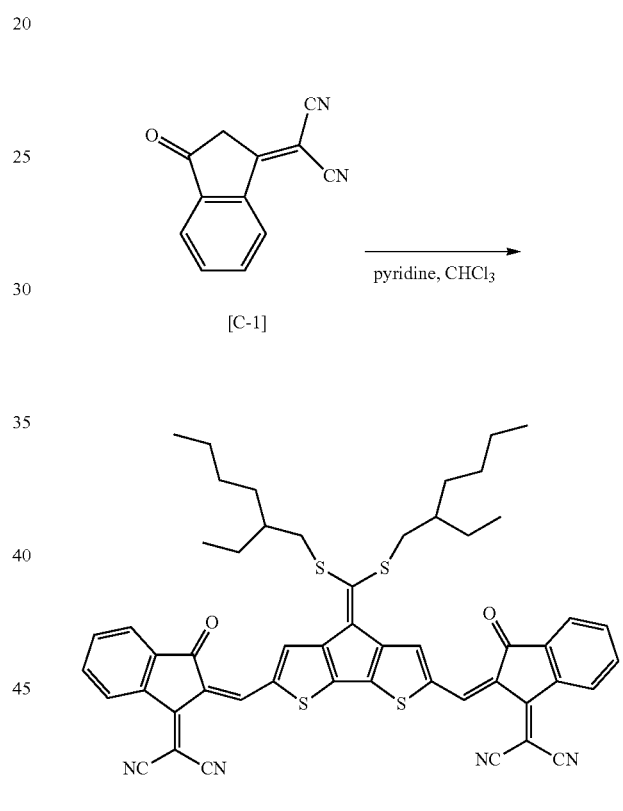

[12]

2 mL of pyridine was added to a solution in which Compound D-2 (0.40 g, 0.75 mmol) and Compound C-1 (1.45 g, 7.5 mmol) were mixed in 15 mL of chloroform (CHCl$_3$) under a nitrogen (N7) atmosphere. After this mixed solution was refluxed under a nitrogen atmosphere for 24 hours, the product was extracted with dichloromethane (CH$_2$Cl$_2$), and washed with water. After the solvent was removed, the residue was recrystallized through methyl chloride (MC)/methanol, and the product was purified through chromatography using a silica gel column using hexane, ethyl acetate, and chloroform (CHCl$_3$) as an eluent. The produced solid was recrystallized through chloroform. Thereafter, the product was washed with methanol and dried under a vacuum condition to obtain 397 mg of Compound 12. (Yield: 60%) (MALDI-TOF MS: 886.2 g/mol)

Preparation Example 13

Preparation of Compound 13

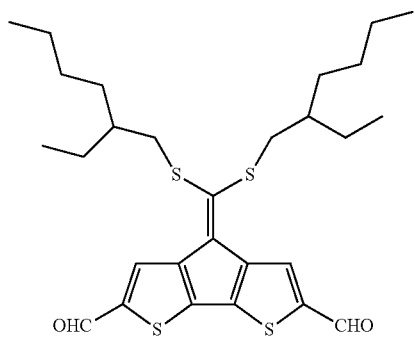

[D-2]

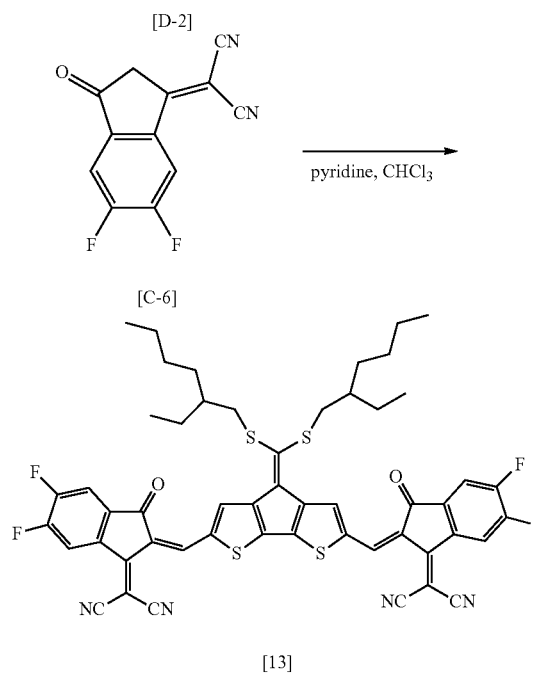

[C-6]

[13]

2 mL of pyridine was added to a solution in which Compound D-2 (0.40 g, 0.75 mmol) and Compound C-6 (1.73 g, 7.5 mmol) were mixed in 15 mL of chloroform ($CHCl_3$) under a nitrogen ($N_2$) atmosphere. After this mixed solution was refluxed under a nitrogen atmosphere for 24 hours, the product was extracted with dichloromethane ($CH_2Cl_2$), and washed with water. After the solvent was removed, the residue was recrystallized through methyl chloride (MC)/methanol, and the product was purified through chromatography using a silica gel column using hexane, ethyl acetate, and chloroform ($CHCl_3$) as an eluent. The produced solid was recrystallized through chloroform. Thereafter, the solid was washed with methanol and dried under a vacuum condition to obtain 453 mg of Compound 13. (Yield: 63%) (MALDI-TOF MS: 958.3 g/mol)

Experimental Example 1

Observation of Change in Color Over Time

Figure 11:
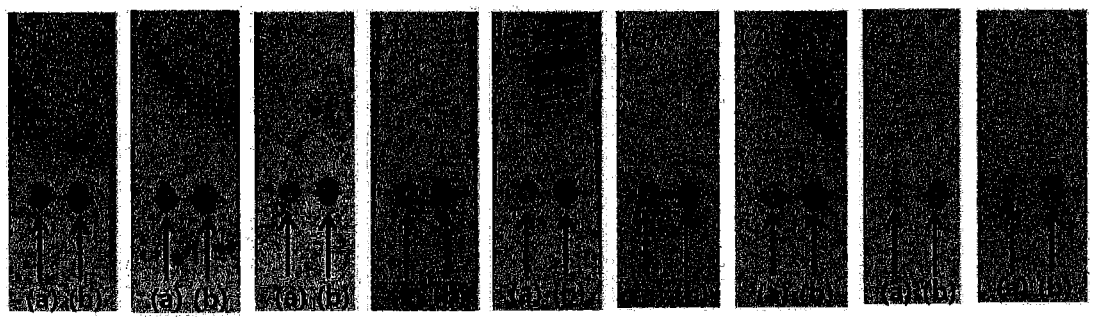
FIG. 11 is a view illustrating color changes of Compound 1 and Compound MC over time.

Solution 1 in which Compound 1 was dissolved in chloroform and Solution 2 in which the following Compound ITIC was dissolved in chloroform were each dropped on a TLC plate. Thereafter, the change in color over time was observed under the air environment. FIG. 11 is a view illustrating color changes of Compound 1 and Compound ITIC over time. Specifically, FIG. 11 illustrates the changes in color right after the solutions were dropped (FIG. 11(1)), after one day passed (FIG. 11(2)), after 5 days passed (FIG. 11(3)), after 7 days passed (FIG. 11(4)), after 8 days passed (FIG. 11(5)), after 11 days passed (FIG. 11(6)), after 14 days passed (FIG. 11(7)), after 25 days passed (FIG. 11(8)), and after 29 days passed (FIG. 11(9)).

In FIG. 11, (a) is Solution 1 in which Compound 1 is dissolved, and (b) is Solution 2 in which Compound ITIC is dissolved.

According to FIG. 11, it can be confirmed that in the case of a solution in which Compound ITIC is dissolved (Solution 2), the change in color occurs as time elapses, whereas in the case of a solution in which Compound 1 is dissolved (Solution 1), the change in color does not occur even though time elapses. Through this, it can be confirmed that the compound according to an exemplary embodiment of the present specification is stable.

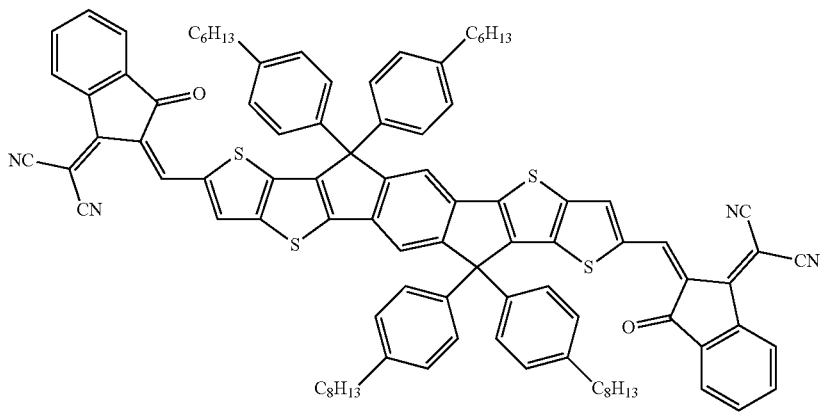

[ITIC]

Experimental Example 2

Manufacture and Performance Evaluation of Organic Solar Cell

Experimental Example 2-1

A composite solution was prepared by dissolving Compound 2 prepared in Preparation Example 2 and Compound. E at a ratio of 1:2 in chlorobenzene (CB). In this case, the concentration was adjusted to 2.0 wt %, and the organic solar cell was made to have a structure of ITO/ZnO/a photoactive layer/$MoO_3$/Ag. A glass substrate coated with ITO was ultrasonically washed using distilled water, acetone, and 2-propanol, and the ITO surface was treated with ozone for 10 minutes, followed by a heat treatment at 120° C. for 10 minutes by spin-coating a ZnO precursor solution. Thereafter, the composite solution of Compound 2 and Compound E was filtered by a 0.45 μm PP syringe filter, and then a photoactive layer was formed by spin-coating the solution. Thereafter, $MoO_3$ was deposited to have a thickness of 5 nm to 20 nm at a rate of 0.4 Å/s onto the photoactive layer in a thermal evaporator, thereby manufacturing a hole transport layer. Ag was deposited to have a thickness of 10 nm at a rate of 1 Å/s onto the hole transport layer in the thermal evaporator, thereby manufacturing an organic solar cell.

[Compound E]

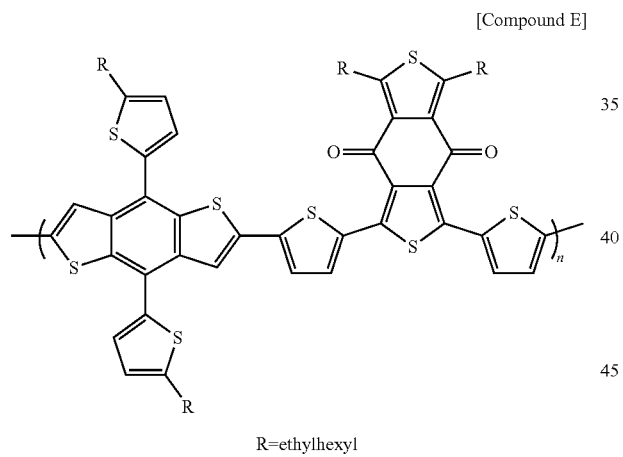

R=ethylhexyl

Figure 12:
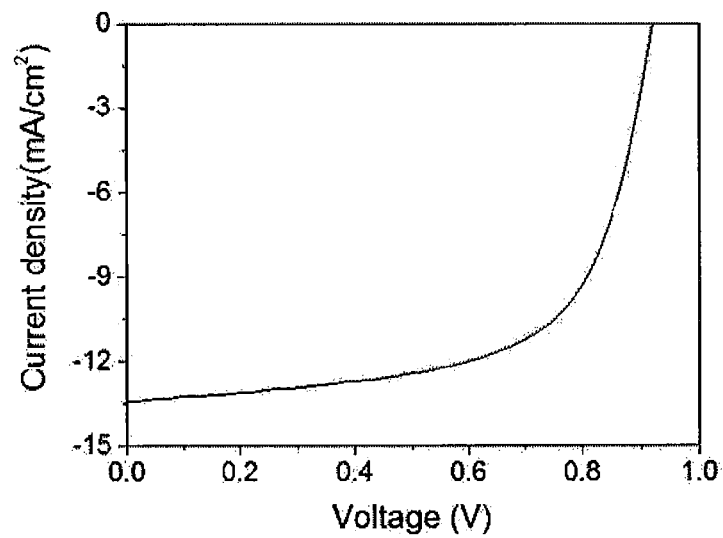
FIG. 12 is a view illustrating a voltage-current curve of an organic solar cell manufactured in Experimental Example 2-1.

The photoelectric conversion characteristics of the organic solar cell manufactured in Experimental Example 2-1 were measured under the condition of 100 mW/cm$^2$ (AM 1.5), and the results are shown in FIG. 12.

Experimental Example 2-2

An organic solar cell was manufactured in the same manner as in Experimental Example 2-1, except that Compound 3 was used instead of Compound 2 in Experimental Example 2-1.

Experimental Example 2-3

An organic solar cell was manufactured in the same manner as in Experimental Example 2-1, except that Compound 4 was used instead of Compound 2 in Experimental Example 2-1.

Experimental Example 2-4

An organic solar cell was manufactured in the same manner as in Experimental Example 2-1, except that Compound 9 was used instead of Compound 2 in Experimental Example 2-1.

Experimental Example 2-5

An organic solar cell was manufactured in the same manner as in Experimental Example 2-1, except that Compound 10 was used instead of Compound 2 in Experimental Example 2-1.

Experimental Example 2-6

An organic solar cell was manufactured in the same manner as in Experimental Example 2-1, except that Compound 11 was used instead of Compound 2 in Experimental Example 2-1.

Comparative Example 1

An organic solar cell was manufactured in the same manner as in Experimental Example 2-1, except that the following Compound F was used instead of Compound 2 in Experimental Example 2-1.

[F]

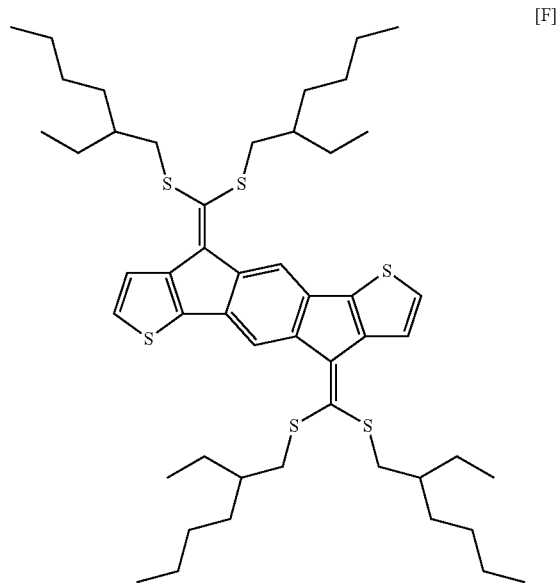 [SMILES: CCCCC(CC)CSC(SCC(CC)CCCC)=C1c2cc3c(cc2-c2sccc21)C(=C(SCC(CC)CCCC)SCC(CC)CCCC)c1ccsc1-3]

Comparative Example 2

An organic solar cell was manufactured in the same manner as in Experimental Example 2-1, except that the following Compound G was used instead of Compound 2 in Experimental Example 2-1.

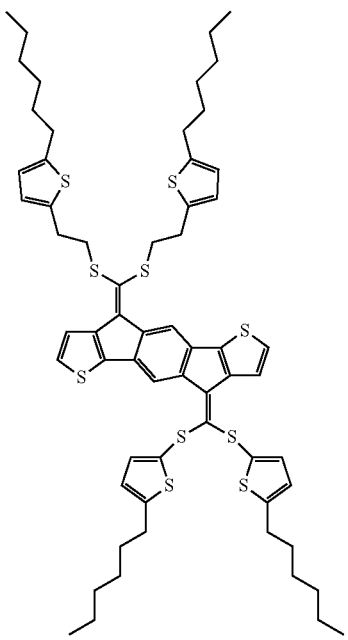

Comparative Example 3

An organic solar cell was manufactured in the same manner as in Experimental Example 2-1, except that the following Compound H was used instead of Compound 2 in Experimental Example 2-1.

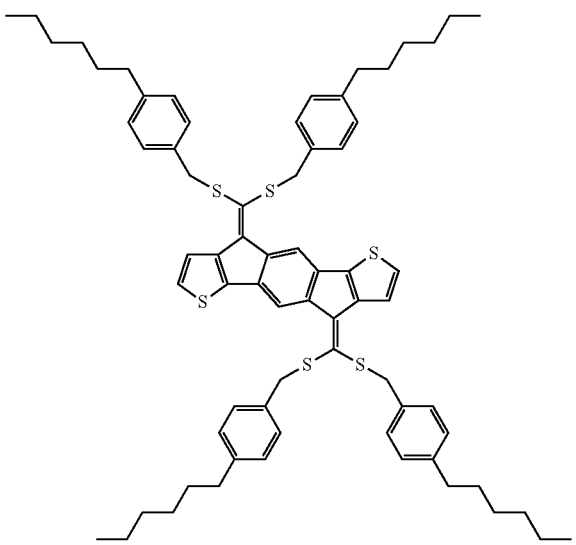

The photoelectric conversion characteristics of the organic solar cells manufactured in Experimental Examples 2-1 to 2-6 and Comparative Examples 1 to 3 were measured under the condition of 100 mW/cm² (AM 1.5), and the results are shown in the following Table 1.

TABLE 1

| Active layer material | | $V_{OC}$ (V) | $J_{SC}$ (mA/cm²) | FF (%) | PCE (%) |
|---|---|---|---|---|---|
| Experimental Example 2-1 | Compound 2/Compound E = 1:2 | 0.81 | 8.28 | 41.2 | 2.76 |
| Experimental Example 2-2 | Compound 3/Compound E = 1:2 | 0.92 | 13.37 | 64.4 | 7.92 |
| Experimental Example 2-3 | Compound 4/Compound E = 1:2 | 0.84 | 12.17 | 53.7 | 5.48 |
| Experimental Example 2-4 | Compound 9/Compound E = 1:2 | 0.81 | 12.92 | 57.6 | 6.02 |
| Experimental Example 2-5 | Compound 10/Compound E = 1:2 | 0.81 | 11.82 | 61.5 | 5.88 |
| Experimental Example 2-6 | Compound 11/Compound E = 1:2 | 0.80 | 10.57 | 62.3 | 5.26 |
| Comparative Example 1 | Compound F/Compound E = 1:2 | 0.075 | 4.41 | 25.5 | 0.084 |
| Comparative Example 2 | Compound G/Compound E = 1:2 | 0.11 | 3.18 | 18.2 | 0.064 |
| Comparative Example 3 | Compound H/Compound E = 1:2 | 0.093 | 4.32 | 17.6 | 0.071 |

In Table 1, $V_{oc}$, $J_{sc}$, FF, and PCE mean an open-circuit voltage, a short-circuit current, a fill factor, and energy conversion efficiency, respectively. The open-circuit voltage and the short-circuit current are an X axis intercept and a Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred.

From Table 1, it can be confirmed that the devices (Experimental Examples 2-1 to 2-6), into which the compound to which the groups (Ra and Rb of Formula 1) that serve as an electron acceptor are applied are introduced, have excellent performance, as compared to the devices (Comparative Examples 1 to 3) to which the compounds (Compounds F, H, and G), which have no group that serves as an electron acceptor, are applied.

The invention claimed is:
1. A compound of Formula 1-1:

[Formula 1-1]

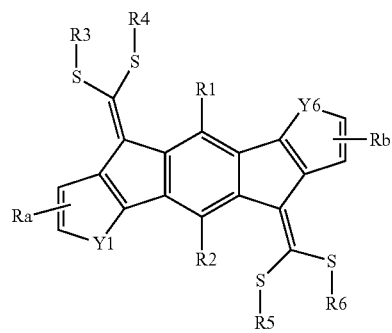

Ra and Rb are the same as or different from each other, and are each independently a group which serves as an electron withdrawing group;
Y1 and Y6 are the same as or different from each other, and are each independently CRR', NR, O, SiRR', PR, S, GeRR', Se, or Te; and R1 to R6, R, and R' are the same as or different from each other, and are each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group.

2. The compound of claim 1, wherein Ra and Rb are the same as or different from each other, and are each any one of the following structures:

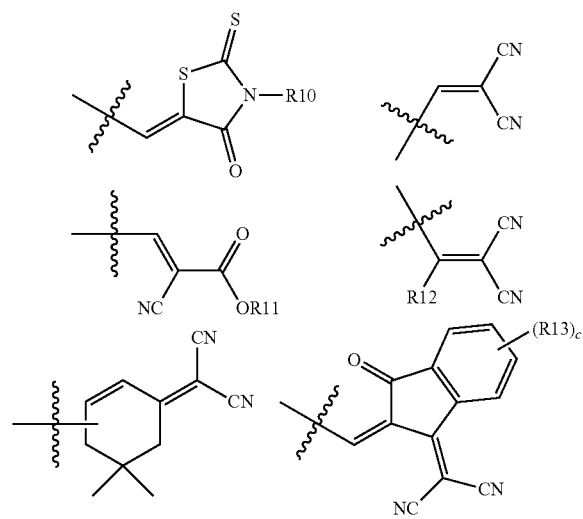

R10 to R13 are the same as or different from each other, and are each independently wherein:

c is an integer from 1 to 4;

when c is 2 or more, each R13 are the same as or different from each other; and hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group.

3. The compound of claim 1, wherein R1 and R2 are the same as or different from each other, and are each independently hydrogen, a halogen group, a substituted or unsubstituted alkyl group, a substituted or unsubstituted alkoxy group, a substituted or unsubstituted aryl group, or a substituted or unsubstituted heterocyclic group.

4. The compound of claim 1, wherein R1 and R2 are hydrogen.

5. The compound of claim 1, wherein the compound of Formula 1-1 is a compound of any one of Formulae 1-12, 1-15, 1-18 and 1-21:

[Formula 1-12]

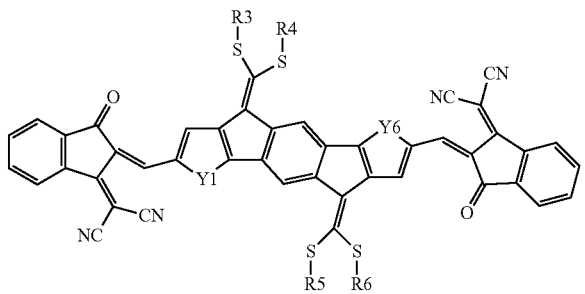

[Formula 1-15]

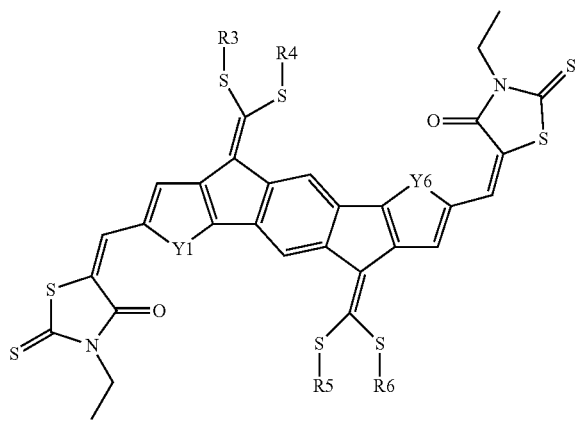

[Formula 1-18]

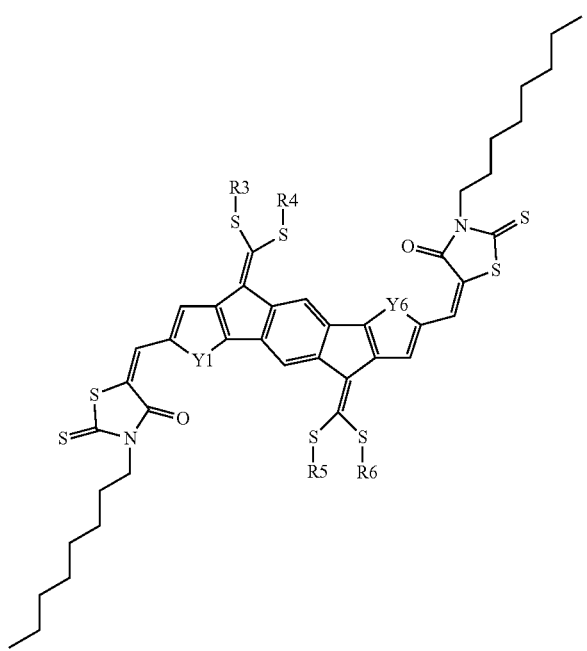

[Formula 1-21]

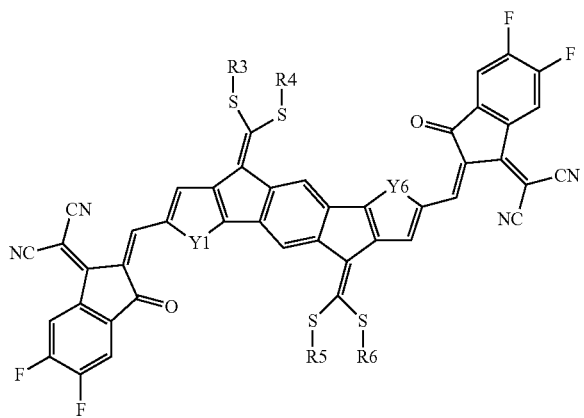

wherein:
Y1 is CRR', NR, O, SiRR', PR, S, GeRR', Se, or Te;
Y6 is CRR', NR, O, SiRR', PR, S, GeRR', Se, or Te; and
R3 to R6, R, and R' are the same as or different from each other, and are each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group.

6. The compound of claim 1, wherein R3 to R6 are the same as or different from each other, and are each independently a substituted or unsubstituted alkyl group, a substituted or unsubstituted aryl group, or a substituted or unsubstituted heterocyclic group.

7. The compound of claim 1, wherein the compound of Formula 1-1 is a compound of any one of the following structures:

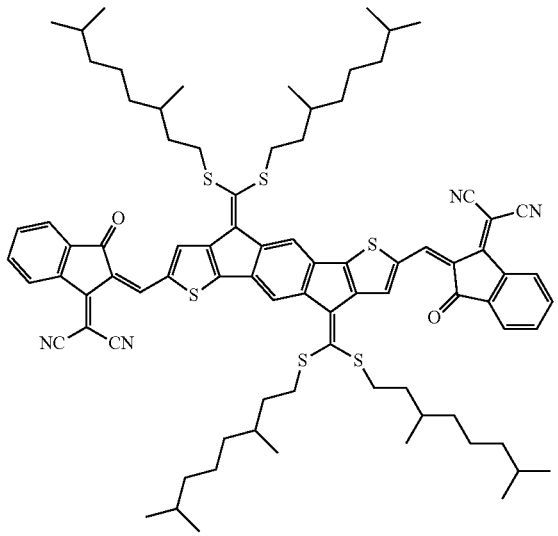

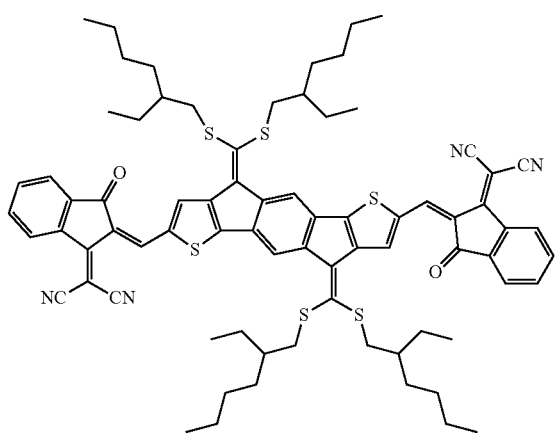

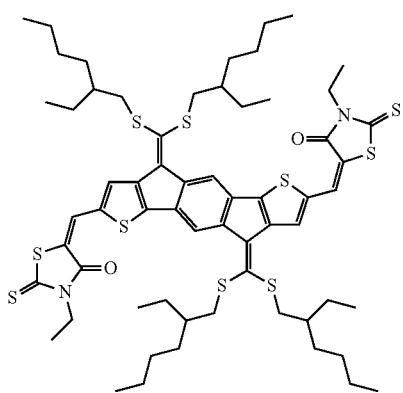

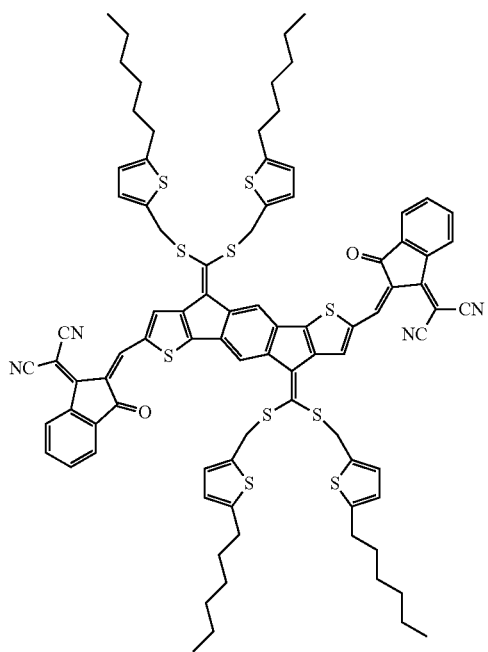

65
66
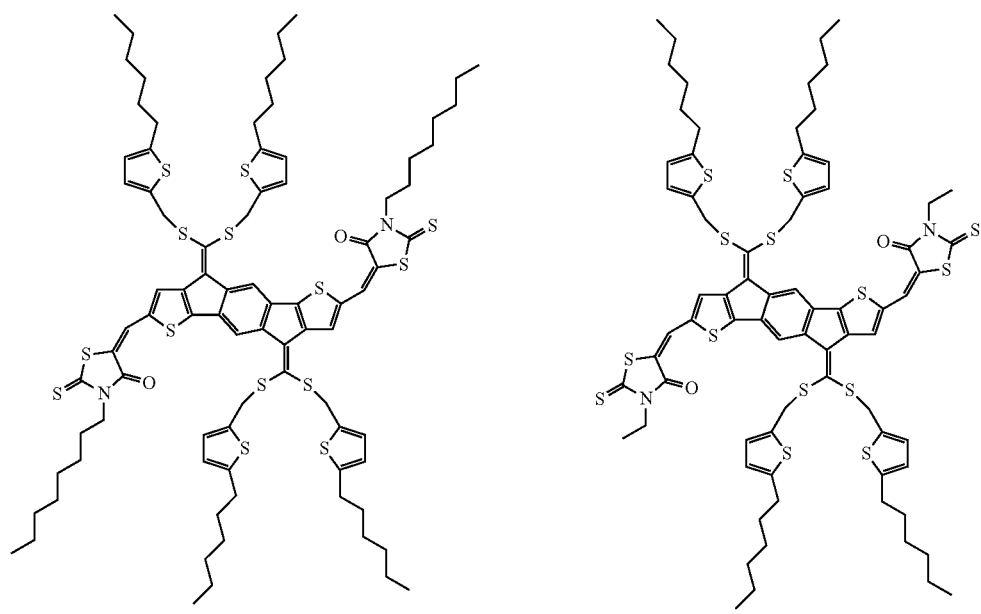
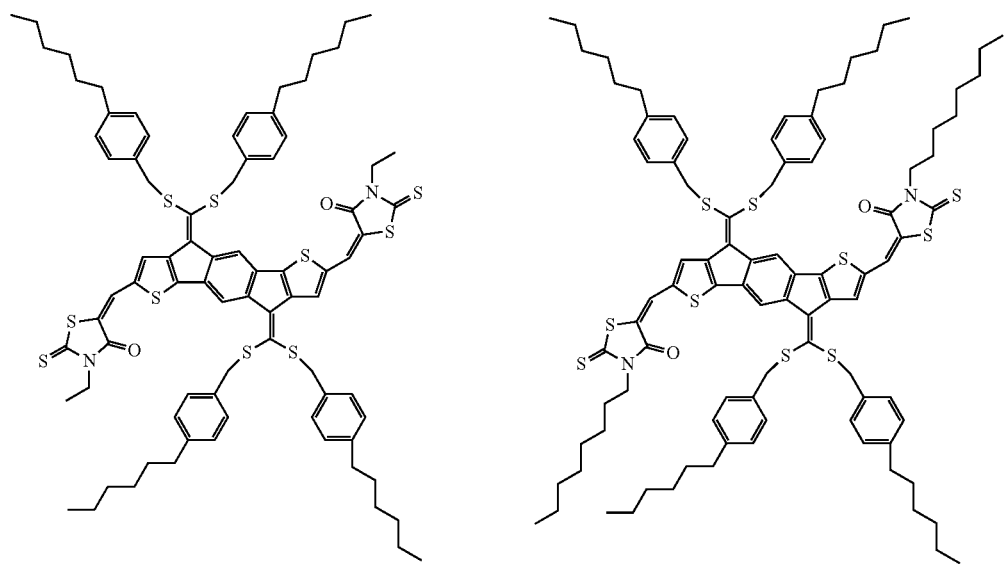

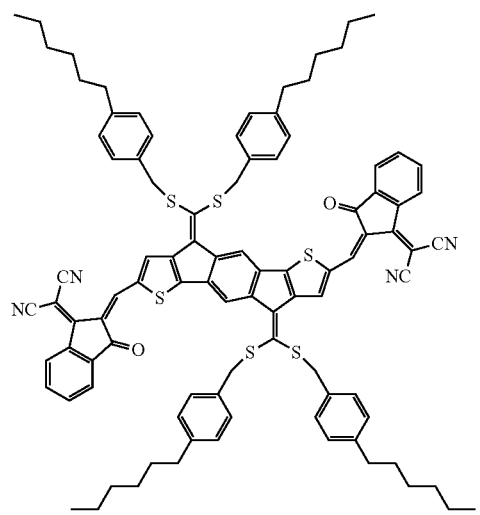
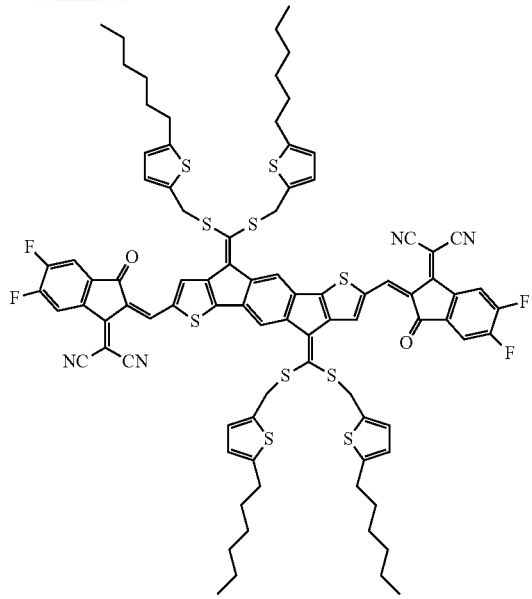
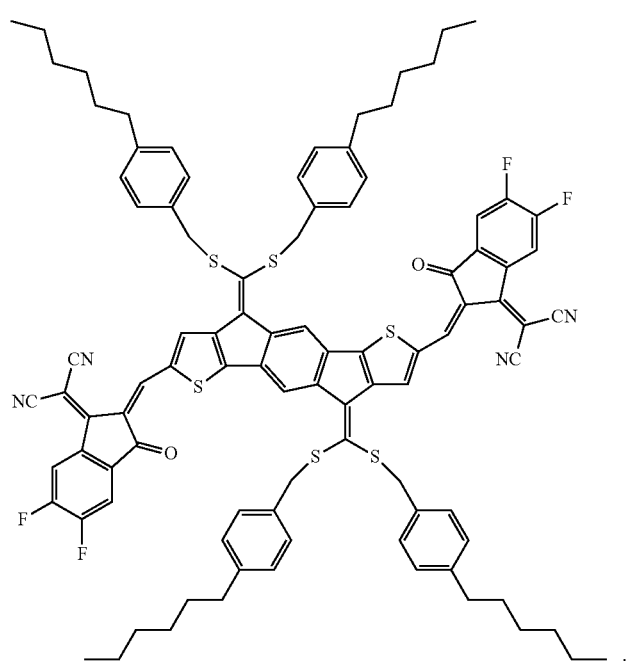

8. An organic solar cell comprising:
a first electrode;
a second electrode facing the first electrode; and
an organic material layer between the first electrode and the second electrode, the organic material layer comprising one or more layers and comprising a photoactive layer,
wherein the one or more layers of the organic material layer comprise the compound of claim 1.

9. The organic solar cell of claim 8, wherein the organic material layer comprises a hole transport layer, a hole injection layer or a layer which simultaneously transports and injects holes, and
the hole transport layer, the hole injection layer or the layer which simultaneously transports and injects holes comprises the compound.

10. The organic solar cell of claim 8, wherein the organic material layer comprises an electron transport layer, an electron injection layer or a layer which simultaneously transports and injects electrons, and
the electron transport layer, the electron injection layer or the layer which simultaneously transports and injects electrons comprises the compound.

11. The organic solar cell of claim 8, wherein the photoactive layer comprises an electron donor material and an electron acceptor material, and
the electron acceptor material comprises the compound.

12. The organic solar cell of claim 11, wherein the photoactive layer comprises a bulk heterojunction comprising the electron donor material and the electron acceptor material, and a weight ratio of the electron donor material to the electron acceptor material is from 1:1 to 1:10.

* * * * *